(12) United States Patent  
Schulter et al.

(10) Patent No.: US 10,123,856 B2  
(45) Date of Patent: Nov. 13, 2018

(54) DENTAL FRAMEWORK AND PROSTHESIS

(71) Applicant: Cagenix, Inc., Memphis, TN (US)

(72) Inventors: Drew Schulter, Memphis, TN (US); Carl Schulter, Germantown, TN (US); Kyle Fraysur, Cordova, TN (US); Daryl Newman, Williston, TN (US); Belal Hamadeh, Memphis, TN (US)

(*) Notice: Subject to any disclaimer, the term of this patent is extended or adjusted under 35 U.S.C. 154(b) by 0 days.

(21) Appl. No.: 15/068,423

(22) Filed: Mar. 11, 2016

(65) Prior Publication Data

US 2016/0270886 A1    Sep. 22, 2016

Related U.S. Application Data

(63) Continuation-in-part of application No. 14/272,566, filed on May 8, 2014.

(51) Int. Cl.

| | |
|---|---|
| *A61C 8/00* | (2006.01) |
| *A61B 6/03* | (2006.01) |
| *A61B 6/14* | (2006.01) |
| *A61C 13/00* | (2006.01) |
| *A61C 13/01* | (2006.01) |
| *A61C 13/34* | (2006.01) |
| *A61K 6/04* | (2006.01) |
| *A61K 6/00* | (2006.01) |
| *A61C 9/00* | (2006.01) |
| *A61B 90/00* | (2016.01) |

(52) U.S. Cl.  
CPC ............ *A61C 8/0027* (2013.01); *A61B 6/032* (2013.01); *A61B 6/14* (2013.01); *A61C 8/0048* (2013.01); *A61C 13/0004* (2013.01); *A61C 13/01* (2013.01); *A61C 13/34* (2013.01); *A61K 6/0017* (2013.01); *A61K 6/04* (2013.01); *A61B 2090/3966* (2016.02); *A61C 8/0001* (2013.01); *A61C 8/0095* (2013.01); *A61C 9/004* (2013.01); *A61C 13/0013* (2013.01)

(58) Field of Classification Search  
CPC ..... A61C 8/005; A61C 8/0012; A61C 8/0027; A61C 8/0077; A61C 9/004; A61C 8/0048; A61C 13/0004; A61C 13/01; A61C 13/34; A61B 6/032; A61B 2090/3966; A61B 6/14  
See application file for complete search history.

(56) References Cited

U.S. PATENT DOCUMENTS

| | | | |
|---|---|---|---|
| 8,100,692 B2 | 1/2012 | Diangelo et al. | |
| 8,764,445 B1* | 7/2014 | DeLuca | A61C 8/005 433/173 |
| 2006/0106484 A1* | 5/2006 | Saliger | A61C 8/0048 700/182 |
| 2011/0136080 A1* | 6/2011 | Holzner | A61C 13/0004 433/201.1 |
| 2012/0052186 A1* | 3/2012 | Junglas | A61C 13/09 427/2.29 |

(Continued)

OTHER PUBLICATIONS

U.S Appl. No. 11/576,450, dated Oct. 23, 2008, Karlsson, Anders.

*Primary Examiner* — Nicholas Lucchesi  
(74) *Attorney, Agent, or Firm* — David J. Kreher

(57) ABSTRACT

A dental prosthesis and a process for design and manufacturing, incorporating a dental implant framework and veneering overlay that will be designed and manufactured simultaneously and permanently fixated to one another.

27 Claims, 28 Drawing Sheets

(56) References Cited

U.S. PATENT DOCUMENTS

2012/0065756 A1* 3/2012 Rubbert ................ A61C 5/007
  700/98
2013/0143178 A1* 6/2013 van Ophuysen ..... A61C 8/0054
  433/173
2016/0242880 A1* 8/2016 Nikolskiy .......... A61C 13/0004

* cited by examiner

DENTAL FRAMEWORK AND PROSTHESIS

CROSS-REFERENCE TO RELATED APPLICATIONS

Ser. No. 14/272,566 May, 2014 Schuler, et al.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC

Not Applicable

AMENDED DESCRIPTION

Field of the Invention

Dentists are continuously searching for methods in which they can provide aesthetic and durable prostheses for their patients. One of the greatest challenges they face are providing a restoration that will resist the occlusal forces in a reduced vertical restorative dimension while obtaining a high level of aesthetics. Dentists are also looking for a cost effective and time efficient manner in which to obtain this result. In application Ser. No. 14/272,566, the Inventor demonstrated a novel dental prosthesis with an implant framework supporting a series of crowns/bridges to provide improved aesthetics and functionality. In one of the embodiments of the invention, the crowns were united together into a bridge due to limitations of the case or for personal preference by the dentist or technician. This bridging provides significant advantages for cases where there is limited restorative space. This application will disclose a new dental prosthesis and design method that provides advantages over current systems and products in the market place and address the challenges of limited restorative space.

Amended Background of the Invention

This application is a continuation in part of U.S. patent application Ser. No. 14/272,566 filed May 8, 2014. The benefit of the earlier filing date of the aforementioned U.S. patent application Ser. No. 14/272,566 is hereby claimed.

Traditional acrylic processed dental hybrid restorations utilize a milled or cast framework/bar where individual denture teeth are retained to the framework by processed acrylic. This process requires a high level of skill and significant time in the laboratory. Many times due to the limited restorative space, these traditional hybrids break and fracture due to the occlusal forces of the patient exceeding the strength of the acrylic. With the introduction of a dental prosthesis consisting of a dental implant framework supporting a series of individual crowns/bridges, the occlusal loads can be transferred through the crown and directly into the supporting framework and dental implants. This individual crown prosthesis has noted improved performance and avoids potential breakdown of the acrylic. However there are instances especially in cases with limited restorative space, where the individual crown prosthesis would not be an ideal option due to the space required for the underlying framework and appropriate wall thickness of crowns. This application will disclose an improved dental prosthesis and design process that will provide improved performance in these spatially limited cases while still achieving the necessary aesthetics for the Dentist and their patients. This application will also disclose a unique CAD subtract body that will be unique in the creation of the dental prosthesis.

In U.S. patent application Ser. No. 14/272,566 Schulter et al. teaches a dental prosthesis consisting of crowns and a dental implant framework intended to mate to a series of implants and abutments.

In U.S. Pat. No. 8,100,692 Diagenlo, et al., teaches a dental framework that is attached to dental anchors, such as dental implants which are secured to the patient's mandible or maxilla, where the framework may be fabricated based on the dimensions and surface contours of a stone cast and diagnostic wax up created from an impression of the patient's mouth.

In U.S. patent application Ser. No. 11/876,450 Karlsson teaches of the utilization of a dental scanning unit commonly found in the market place.

AMENDED SUMMARY OF THE INVENTION

In accordance with the first embodiment of the invention, a dental prosthesis is disclosed consisting of a veneering overlay and dental implant framework intended to mate to a series of implantsand abutments in a patient's mouth. The veneering overlay and dental implant framework are designed on the basis of digital data defining the appropriate tooth contours, gingiva contours, and implant locations. The dental implant framework consists of a series of mating cylinders, support posts. The veneering overlay duplicates the anatomy provided in the digital data defining the appropriate tooth position and gingiva contours of the final prosthesis. The veneering overlay and dental implant framework are designed simultaneously and with a predefined mating surface and clearance gaps to ensure the appropriate mating of the veneering overlay to the dental implant framework. The unique mating surface is created through a unique CAD subtract body that is dependent upon the design features of the dental implant framework. The veneering overlay and dental implant framework are permanently fixated to one another in providing the completed dental prosthesis.

In accordance with the second embodiment of the invention, a dental implant framework is disclosed which is intended to mate to a veneering overlay and a series of implants and abutments in a patient's mouth. The dental implant framework is designed on the basis of digital data defining the appropriate tooth contours, gingiva contours, and implant locations. The dental implant framework consists of a series of mating cylinders, support posts. The dental implant framework is designed with a predefined mating surface and clearance gaps to ensure the appropriate mating of the veneering overlay to the dental implant framework. The unique mating surface is created through a unique CAD subtract body that is dependent upon the design features of the dental implant framework.

In accordance with the third embodiment of the invention, a unique CAD subtract body is disclosed to create the mating surface for a veneering overlay and a dental implant framework. The veneering overlay and dental implant framework are designed on the basis of digital data defining the appropriate tooth contours, gingiva contours, and implant locations. The dimension of the unique CAD subtract body are dependent upon the dimension of the dental implant framework. Some of the dimensions of the unique CAD subtract body are used in creating the mating surface for the veneering overlay to mate with the dental implant framework, where other dimensions are used in creating clearance gaps between the veneering overlay and dental implant framework. The unique CAD subtract body is fully parametric and can be updated per the unique requirements of the patient, dentist, or technician.

AMENDED DETAILED DESCRIPTION OF THE INVENTION

The dental prosthesis is supported by a dental framework which functions as a structural support and point of attachment. The dental framework is attached to dental anchors, such as dental implants which are secured to the patient's mandible or maxilla, the framework may be fabricated based on the dimensions and surface contours of a stone cast and diagnostic wax up created from an impression of the patient's mouth such as described in U.S. Pat. No. 8,100, 692. The stone cast replicates the soft tissue contours and implant positions in the patient's mouth. The diagnostic wax up represents the final prosthesis and ultimately the position of the denture teeth to be restored for the patient. In order to create the diagnostic wax up, the dentist or technician will position upon the stone cast the stock denture teeth and wax as required for proper prosthetic function and aesthetics. The commercially available stock teeth are generally manufactured with predetermined geometries of a typical given tooth in various sizes by a third-party manufacturer.

Figure 1:
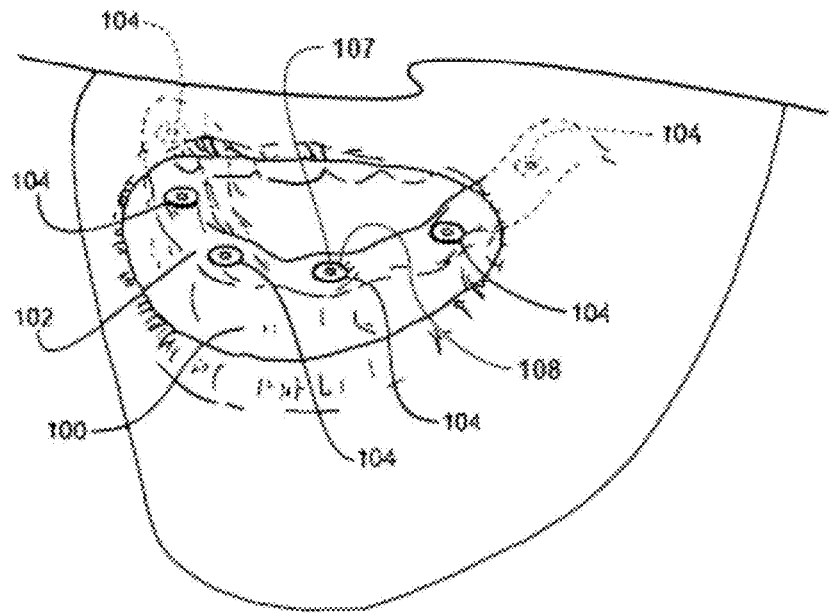
FIG. 1 is a fragmentary perspective view of a patient's open mouth with the anchors embedded in the patient's mandible.

Retention of the dental prosthetic requires anchors secured in the patient's mouth. In FIG. 1, the patient's jaw or mandible 100 can be seen overlaid with soft mucosal tissue 102 (For the purposes of this description, the inventor will be utilizing the term mucosal tissue or soft tissue to describe any of the soft tissue found in the oral cavity, which may include but not limited to mucosal, gingiva, or alveolar tissue.). An anchor 104, also known as an "implant" or "fixture" is shown embedded into the patient's mandible 100. This anchor is retained within the bone of the mandible by a screw thread. It is driven into the mandible 100 by coupling a wrench or similar device to the top of the anchor 104 and rotating the wrench to drive the anchor into the jaw bone just as one would drive a screw into a piece of wood. In an alternative embodiment, the anchor 104 is press fitted into a hole formed with a drill, reamer, broach, osteotome, or similar device.

FIG. 1 illustrates the first step in the process, that of forming an opening in the mandible of the patient and fixing an anchor therein, while leaving a top surface of the anchor exposed above mucosal tissue 102 for mating (coupling) to and supporting a dental prosthesis or restorative component such as a denture, bridge, crown, framework, abutment, healing cap, or coping (hereinafter referred to as "denture"). Note that while the process illustrated herein describes and illustrates a mandible for illustration purposes, the same process is performed to embed anchors 104 into the patient's maxilla and create dental prostheses for the maxilla.

To attach anchors 104, the dentist first makes an incision in the mucosal tissue 102 where a missing tooth or teeth would normally extend from the mandible where it is embedded, through the gum, and into the oral cavity. Once the incision is made, the dentist makes a hole (which may include such processes as drilling, broaching or reaming) in the mandible 100 in the same general direction and location as the missing tooth. The dentist then fixes an anchor 104 into the hole thus created and sutures the incision, typically leaving mating surface 108 of anchor 104 exposed while the bone osseointegrates to the outer surface of anchor 104. Alternatively, the dentist may attach a healing cap to the anchor 104 and suture the gum around or over the top of the anchor 104 and the healing cap, permitting the gum to heal around or over the top of the anchor 104 as it osseointegrates. In this alternative process, once the anchor has osseointegrated, the dentist incises the mucosal tissue 102 extending over the top of the now-integrated anchor 104 and retracts the mucosal tissue to each side, exposing the mating surface 108 of anchor 104 and permitting the mucosal tissue to heal.

Figure 2:
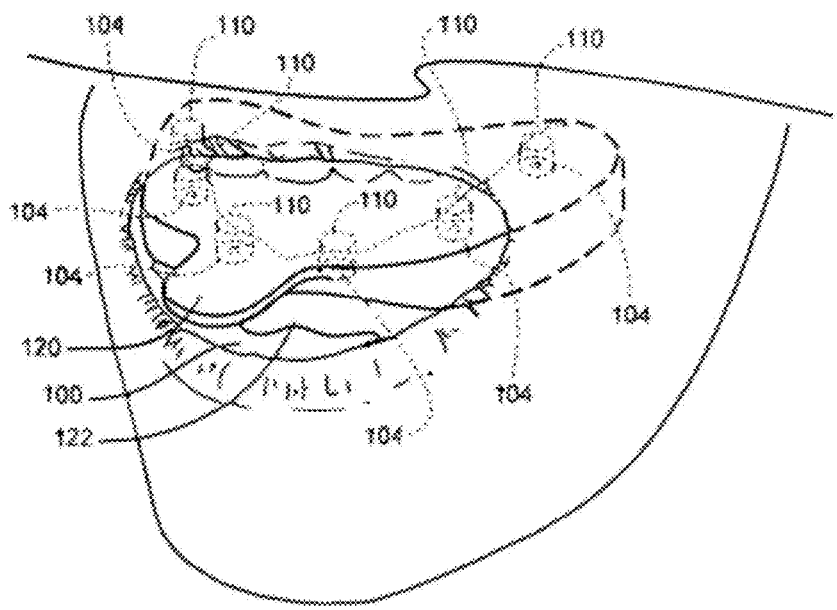
FIG. 2 is a fragmentary perspective view of the patient's open mouth with several copings attached to the anchors and an impression tray with impression material surrounding the patient's mucosal tissue and submerging the copings.

The anchor 104 has a central longitudinal aperture 107 in the top which is configured to receive an impression coping 110, as shown in FIG. 2, (or a fastener configured to mount the impression coping 110) that is affixed to the anchor 104. This coping transfers the size, shape, location or orientation of the mating surface 108 of the anchor (and preferably all four) to the stone cast (see below). It is the mating surface 108 that is oriented to the finished denture, and hence the mating surface 108 from which the structures of the denture that mount to the anchors are derived. In general, anywhere from one to twelve of these anchors are embedded in the jaw and are provided as mounting points for the denture. In an alternative configuration, anchor 104 may have a variety of configurations on its mating surface 108 including threaded or unthreaded protrusions or recesses that are configured to engage a denture. The use of an anchor 104 having a central aperture and internal threads for engaging a coping is a matter of convenience herein and should not suggest that the process is limited to an anchor having this configuration.

Mating surface 108 is typically the surface on which the denture will be mounted or a surface having a predetermined position with respect to that surface on which the denture will ultimately be mounted. The coping 110 is configured to engage surface 108 and surrounding structures of anchor 104 (if any) such as holes that extend into (or protrusions that extend above) the surface 108.

These inter engaging surfaces of coping 110 and anchor 104 serve to align the coping and the anchor in predetermined positions with respect to each other when fixed together, such that if one knows the position and orientation of surfaces on the coping one can know the position and orientation of corresponding structures on the anchor 104 and more preferably when a scanner (see below) determines the position and orientation of structures on copings 110 it can mathematically determine the position and orientation of corresponding structures on anchors 104. Anchor 104 is preferably cylindrical and has a longitudinal axis 111, as does coping 110. In a typical arrangement, when the coping 110 is fixed in its predetermined position with respect to anchor 104, a longitudinal axis 111 of the coping is coaxial with the longitudinal axis of the anchor 104. The coping 110 and the anchor 104 are preferably threadedly engaged to permit surfaces on the coping to be drawn down tightly against mating surface 108 for precise alignment of their inter engaging surfaces. Alternatively, the coping 110 and anchor 104 to which it is coupled may be equipped with inter engaging snap fastening connecting surfaces that hold the coping in the proper orientation with respect to anchor 104.

In FIG. 1, the edentulous mandible 100 has six anchors 104 affixed therein in a spaced-apart relation extending from the front of mandible 100 around each side. The anchors 104 are disposed in a generally upright and parallel relation extending into the top surface of mandible 100. The dentist attaches corresponding copings 110 to the top of each anchor 104 and extends upward in a generally upright and parallel relation to the other copings 110. The application illustrated herein shows the use of six anchors configured to support a denture. Other applications with more or fewer anchors 104 are possible. Furthermore, the mandible need not be edentulous (shown here), but may have, and often does have, one or more natural teeth remaining in the maxilla or mandible between which the anchors 104 are embedded to support one or more dentures (such as fixed or removable partial dentures) to fill the gap or gaps between the existing natural teeth. In this case, the anchors would not be spaced evenly about the mandible, as shown here, but would be spaced irregularly in the gaps created by the absence of natural teeth.

FIG. 2 illustrates the next step in the process of creating a denture, the step of creating an impression of the patient's mandible. This figure shows an impression tray 120 filled with flexible impression material 122. The tray is a semi flexible plastic structure that holds the impression material 122 in position around the patient's teeth (if any) and mucosal tissue. FIG. 2 shows a tray 120 for the lower teeth surrounding teeth, mucosal tissue, and mandible of the patient.

The copings 110 previously attached by the dentist to the anchors 104 are completely submerged by the dentist in impression material 122 such that the entire outer surfaces of the copings 110 extending above the surface of the mucosal tissue on the patient's mandible 100 are completely covered. The impression material is left in this position to set. Once set, the individual copings 110 are fixed with respect to each other in the same position and orientation that the anchors 104 are fixed with respect to each other. The curing process fixes the copings in this position and thereby permits the copings to be collectively removed together with the impression material while preserving their orientation.

In the next step of the process, the dentist flexes the tray 120 and the now set impression material 122 and removes them from the patient's mouth. Enough impression material 122 is placed in the tray and disposed around the patient's mandible 100 to cover any still-existing teeth of the mandible and the mucosal tissue 102 of the mandible as well as the copings 110.

When the tray 120 and impression material 122 are removed, the copings are removed with them, embedded in the now-cured impression material 122. The process of removal disconnects the copings 110 from the anchors 104, permitting the copings to be removed while still embedded in the impression material 122. If the copings include a threaded portion that holds them to the anchors, this threaded portion is unthreaded from the anchors. If the copings are fastened to the anchors with a snap fastening portion, the snap fastening portions are unsnapped from each other. The now-cured impression material 122 that couples the copings 110 to each other preserves the relative positions and orientations of the mating surfaces of all the copings 110 and hence relative positions and orientations of the mating surfaces 108 of all the anchors 104 with respect to each other. This relationship is preserved in the relative positions and orientations of the surfaces of copings 110 that were connected to the mating surfaces 108 of anchors 104. To even further ensure the preservation of this relationship, some dentists will attach the copings 110 to one another by applying a light cured acrylic material prior to submerging them in the impression material 122. The impression material 122 in which copings 110 are embedded also preserves the surface contours of the mucosal tissue and the remaining teeth (if any) in the mandible and their relative positions with respect to the mating surfaces of copings 110 and anchors 104. The surface of the impression material 122, once removed from the patient's mouth, is a negative replica of the soft tissue and teeth. The surfaces of copings 110, now separated from anchors 104 and exposed on the inside surface of the impression material 122, are a negative replica of surfaces 108 of anchors 104 to which they were coupled. The now-cured impression material 122 is therefore a negative replica of all the free surfaces, including teeth, mucosal tissue, and the surfaces of the copings embedded in the impression material are a negative replica of the mating surfaces 108 of anchors 104. The cured impression material with embedded copings is commonly called an "impression" and identified in the figures herein as item 123.

Figure 3:
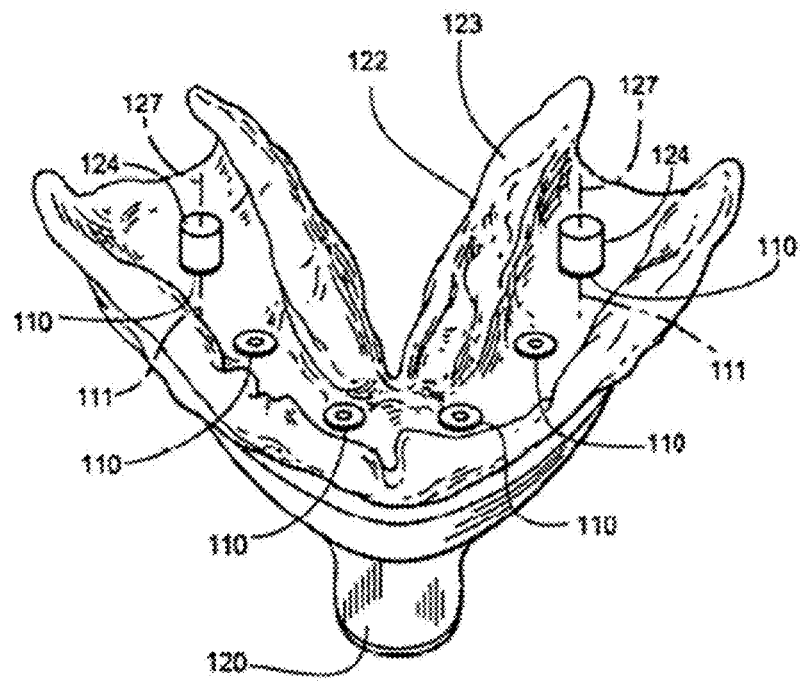
FIG. 3 is a perspective view of the impression of FIG. 2 inverted and removed from the patient's mouth with two analogs attached to two of the copings.

FIG. 3 shows the impression 123 inverted and removed from the patient's mouth. In this embodiment, there are six copings 110 embedded in the impression 123. The bulk of the copings 110 are embedded in the impression 123. Only the very ends of the copings 110 extend upward and out of the impression 123 (in this inverted orientation).

In FIG. 3 the dentist has begun the next step of the process, that of attaching analogs 124 to the exposed surfaces of all of the copings 110. Analogs 124 are structures that replicate the anchors 104. As in the case of the copings themselves, each analog 124 preferably comprises a generally cylindrical body with a longitudinal axis 127 that is coaxial with the longitudinal axis 111 when attached to coping 110.

The end surfaces of analogs 124 are configured to abut and mate with the free surfaces of the copings 110 that were previously coupled to anchors 104 and normally attach in the same manner as copings 110 to anchors 104. The surfaces of analogs 124 replicate the position and orientation of mating surfaces 108 of anchors 104. In effect, the spacing and orientation of anchors 104 was transferred to the copings 110, and transferred back again to analogs 124, which have the same spacing and orientation as the anchors 104. Thus, each analog 124 is coaxial with and is disposed in the same position as anchor 104.

Figure 4:
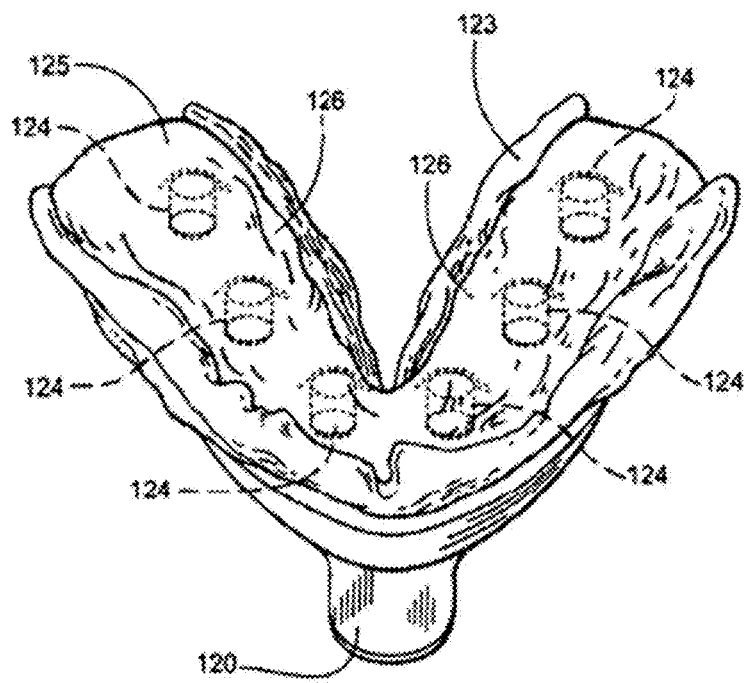
FIG. 4 is the same perspective view of FIG. 3, but with analogs attached to all the copings, and the impression filled with dental stone material and the analogs submerged in the dental stone material.

In the next step of the process, illustrated in FIG. 4, the dentist pours a mixed dental stone material 126 into the cavity in impression 123 that was formed by the patient's mandible, submerging all of the analogs 124. Stone material 126 covers the exposed portion of the analogs 124 as well as the surfaces of impression 123 formed by the patient's mucosal tissues and teeth. Once filled into impression 123, the stone material 126 is then permitted to harden to a rock-like consistency, creating a structure that is called a "stone cast" 125.

Figure 5:
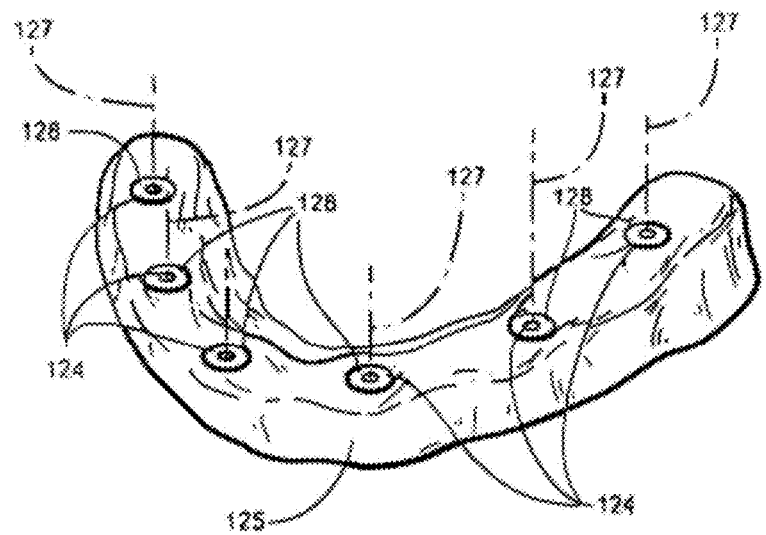
FIG. 5 is a perspective view of the stone cast formed by the dental stone material poured in the impression of FIG. 4 in its hardened state, inverted, and with the impression removed showing the analogs with the analog surfaces that mated with the copings (in FIG. 4) now exposed.

FIG. 5 represents the next step of the process which the dentist performs once the stone material 126 has hardened. The dentist removes impression 123 from the stone cast 125, leaving the stone cast 125 with the analogs embedded therein. The stone cast 125 positively replicates the position and orientation of mating surfaces 108 of anchors 104, which are represented in the stone cast 125 by the mating surfaces 128 of the analogs 124 that were fixed to the free ends of copings 110 (FIG. 3). The portions of the stone cast 125 surrounding analogs 124 positively replicates the surface of the mucosal tissues of the mouth, which were transferred from the mucosal tissues of the mouth to the impression as a negative replica and then back to the stone cast as a positive replica of those tissues. The stone cast 125 also replicates the surface of the patient's existing teeth (not shown). When the patient has existing teeth, the position and orientation of the surfaces of the teeth are transferred first to the impression as a negative replica and then to the stone cast as a positive replica. In the present embodiment, the mandible 100 is edentulous and therefore there are no existing teeth.

As will be explained later, teeth that are replicated in impression 123 and stone cast 125 provide a precise reference to indicate the location of the jawbone. The soft tissues that are replicated in the impression 123 and stone cast 125 can change their position due to swelling, edema, injury, irritation, or damage to the mouth. Teeth, since they are much harder and are embedded in the jawbone, provide a more stable reference, over time, of the position of the jawbone and thus indirectly, of the position and orientation of anchors 104.

The impression molding and stone casting processes described above provide accurate replicas of the position and orientation of the mating surfaces 108 of anchors 104, the mucosal tissues, and the teeth.

In the preferred embodiment, the mating surfaces 108 of anchors 104 are exactly duplicated by the mating surfaces 128 of the analogs 124: they are in exactly the same position and at exactly the same orientation. In an alternative embodiment, the mating surfaces 128 on the analogs may be offset slightly or configured slightly differently than the mating surfaces 108 of anchors 104. In some cases, manufacturers choose to make analogs or other connecting components that have mating surfaces slightly different from the mating surfaces 108 of the anchors 104 for example to permit the copings 110 to be more easily attached to anchors 104 or to permit analogs 124 to be more easily attached to copings 110. Any slight difference in position such as this is intentional, however, and is eliminated later in the process when the denture is created so that the mating surfaces of the denture are precisely oriented to mate properly with surfaces 108 of anchors 104 in the patient's mouth.

Further, the anchors 104 in the patient's mouth may not be connected directly to the dental framework. Abutments may be mounted on the anchors 104 (i.e. the anchors have surmounted abutments). The dental framework may be mounted to these abutments, and thus indirectly mounted to anchors 104. When the dental framework being designed is intended to be mounted on abutments mounted on anchors 104, the analogs 124 may be provided with surmounted abutments, i.e. the analogs may include the abutment design incorporated into it, to replicate the mating structure of the abutment to the framework.

While the mating surfaces 128 of the analogs 124 and the mating surfaces 108 of anchors 104 may be slightly differently configured, the longitudinal axes of each of the anchors 104 and the analogs 124 are preferably identically oriented and spaced apart, each pair of corresponding analog and anchor sharing a common longitudinal axis (i.e. they are coaxial). Considered differently, if the surface of the stone cast representing the soft tissues and teeth of the patient's mouth could be superimposed on top of the patient's mucosal tissues 108 that formed the stone cast 125, all the longitudinal axes defined by the analogs would be superimposed on (i.e. simultaneously coaxial with) all the corresponding axes defined by the anchors. The longitudinal axes 127 of the analogs 124 and the surfaces of the stone cast 125 defined by the mucosal tissues 108 the patient are positive replicas of the longitudinal axes 111 of anchors 104 and the surfaces of mucosal tissues 108.

The replica of any teeth formed in the surface of the stone cast are formed with respect to one another and with respect to the analogs such that they duplicate the position of any existing real teeth in the patient's mouth with respect to one another and with respect to mating surfaces 108 and longitudinal axes of the anchors 104 in the patient's mandible. The replica of the mucosal tissues formed in the surface of the stone cast are in generally the same position on the stone cast as they are in the patient's mouth including the replication in the stone cast 125 of the junction between the mucosal tissue and any existing teeth and anchors 104, as well as a replication in the stone cast of all the mucosal tissue that will be covered by the denture.

Once the dentist has created the stone cast 125, which is a positive replica of the patient's jaw, including replication of existing teeth, mucosal tissue, and anchors, the dentist then proceeds to the next step in the process: designing and creating the denture that will be fitted to the patient's mouth (in this case, the patient's jaw).

The dentist or technician manually creates a diagnostic wax-up 130 of the desired denture teeth position and occlusal orientation, using flexible molding materials such as wax, acrylic, or other polymers and stock denture teeth commonly found in the market. These stock denture teeth are of a known dimension and have contours specific to the mold or catalog number of the denture teeth. These denture teeth are also made from a combination of materials such as acrylic and composite. The composite portion is typically used for the aesthetic upper portion of the denture tooth as the composite can provide the appearance of translucency. The lower portion of the denture tooth typically consists of acrylic which is ideal in bonding to the processed acrylic for the denture base or acrylic used in adhering the denture teeth to a milled or cast framework/bar for a traditional hybrid dental restoration. The dentist or technician may also modify these denture teeth slightly in order to provide the appropriate occlusal scheme to best fit any existing teeth or dental prosthesis on the opposing arch. These modifications may include but are not limited to the addition of occlusal contours by adding wax or the removal of occlusal contours by modifying the surface with a bur and hand piece.

The diagnostic wax-up 130 is created to verify the proper location of the denture mucosal tissue and denture teeth with respect to the patient's actual mouth to ensure proper tooth orientation, and to ensure that the location and placement of the denture within the patient's mouth restores form, fit and function. In short, the diagnostic wax-up 130 is a model of and looks like the denture that is ultimately produced, but is made of softer materials to permit it to be adjusted and adapted until the patient and dentist are pleased with its form, fit, function and aesthetics.

The dentist creates the wax-up 130 on the stone cast 125, building it up on the patient's replica mucosal tissue. When the dentist is finished making the wax-up 130, he removes the wax-up 130 from the stone cast 125, and places it into the patient's mouth so the patient can see, firsthand, what the denture or prosthesis will look like when it is finished. If the wax-up 130 fits, the patient can bite properly, and the patient is pleased with the appearance of the wax-up 130, the dentist then proceeds to manufacture the framework and resulting prosthesis.

Figure 6:
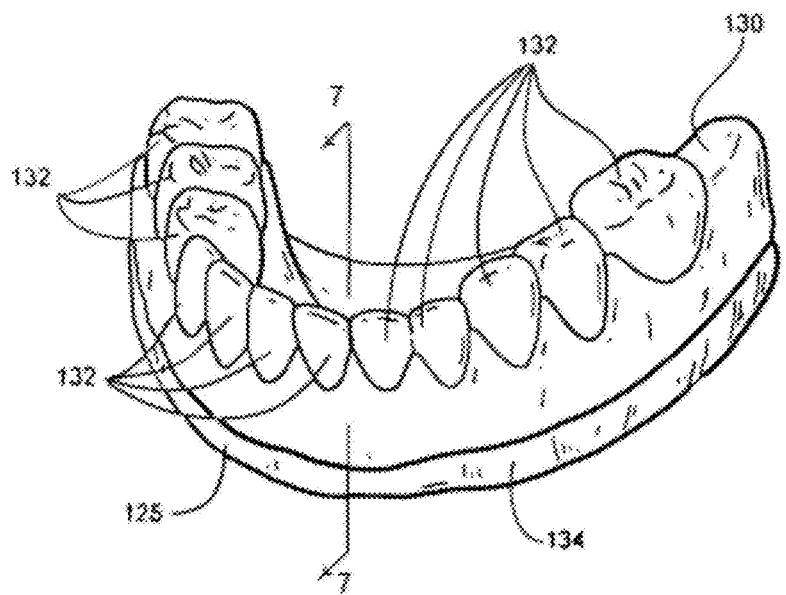
FIG. 6 is a perspective view of the stone cast of FIG. 5 with the dentist's fabricated diagnostic wax-up built up on the stone cast and abutting the analogs.
Figure 7:
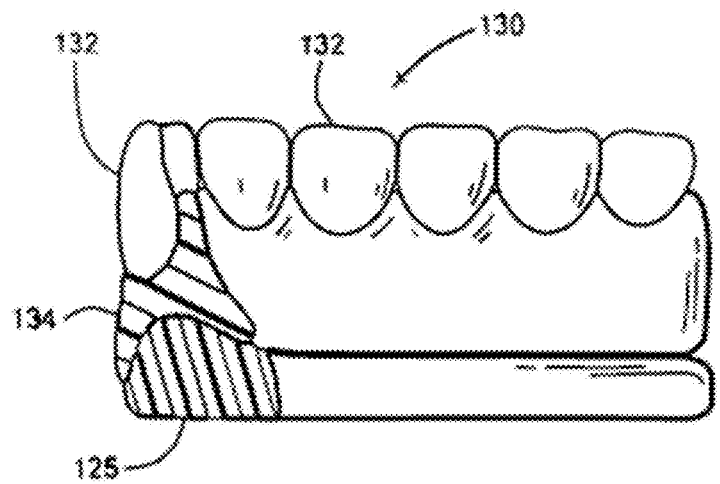
FIG. 7 is a cross-sectional view of the stone cast of FIG. 6 taken at section line 7-7 in FIG. 6.

FIGS. 6-7 illustrate the process of creating a wax-up, showing the stone cast 125 as it would appear with a wax-up 130 modeled on its outer surface. In FIG. 6, the stone cast 125 is shown covered with the wax-up 130 which comprises the denture teeth 132 embedded in wax 134 which the dentist has molded directly to the surface of the stone cast 125. FIG. 7 is a cross-sectional view through the stone cast 125 plus wax-up 130 shown in FIG. 6. This cross-section is taken at section line 7-7 in FIG. 6. Once the dentist has created the wax-up 130 and has verified the fitting of the wax-up 130 in the patient's mouth, he can then begin the process of having the framework fabricated for the patient. Traditionally these frameworks have been cast, but more recently it has become common for these frameworks to be scanned and duplicated in an appropriate dental material (titanium, cobalt chrome, zirconia, plastic, PMMA, acrylic, etc. . . . ) by a common manufacturing method (milling, 3D printing, laser sintering, EDM, etc. . . . )

Figure 8:
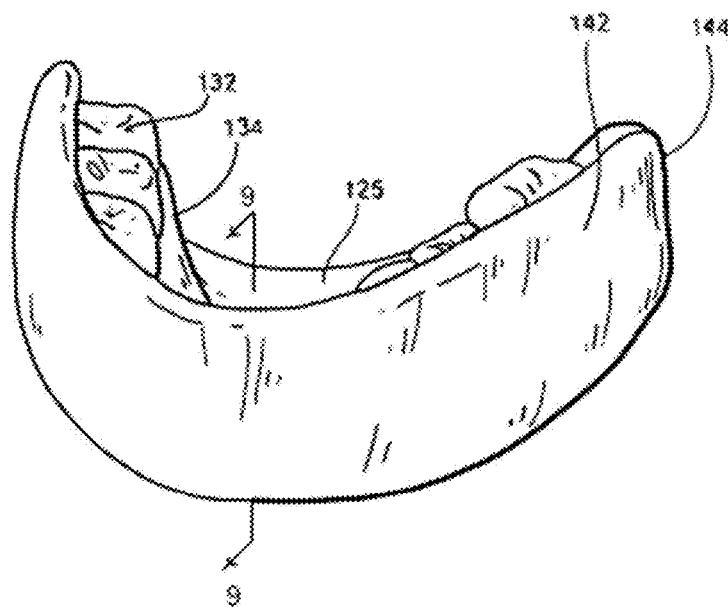
FIG. 8 is a perspective view of the stone cast of FIGS. 5-7, with a putty index molded to the facial aspect of the diagnostic wax-up.
Figure 9A:
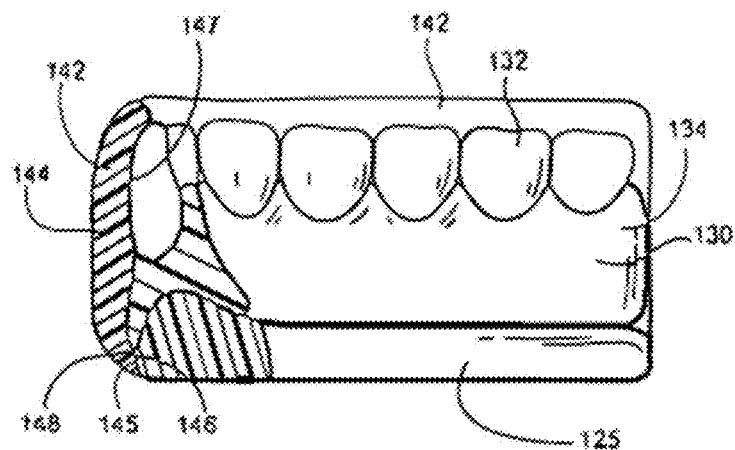
FIG. 9A is a cross sectional view of the stone cast of FIGS. 5-8 taken at section line 9-9 in FIG. 8.
Figure 9B:
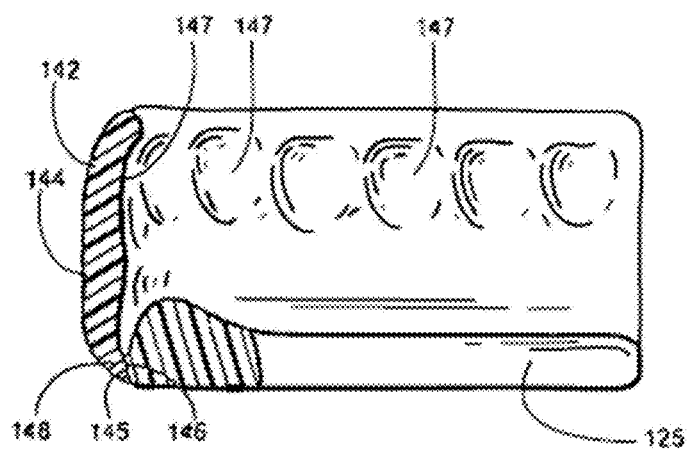
FIG. 9B is a cross sectional view of the stone cast of FIGS. 5-8 with the diagnostic wax-up removed to show the inner surface of the putty index and the impression of the facial aspect of the diagnostic wax-up formed on the inner surface of the putty index.
Figure 10A:
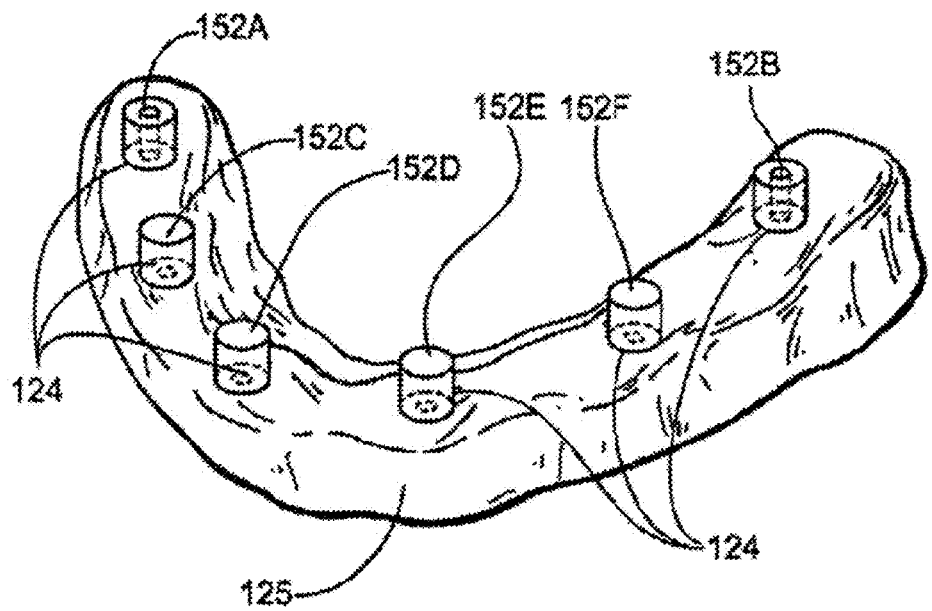
FIG. 10A is a perspective view of the stone cast of FIGS. 5-9B with six fittings, one fitting attached to each of the six analogs.
Figure 10B:
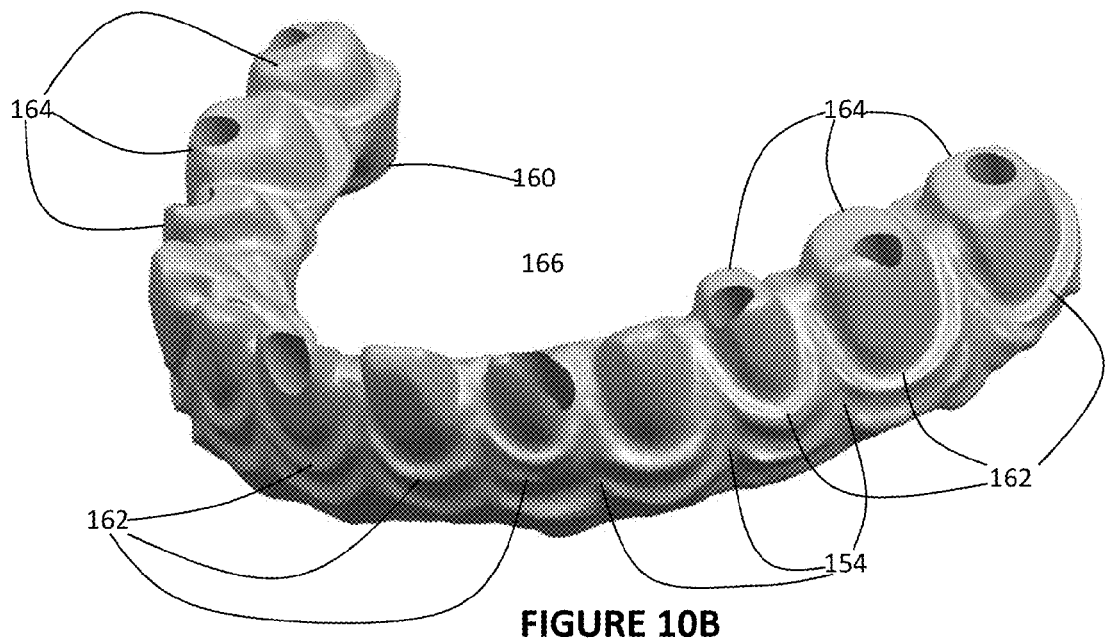
FIG. 10B is a perspective view of the bridging structures fixed to and between each of the six fittings to form a wax-up framework mounted on the six analogs.
Figure 11A:
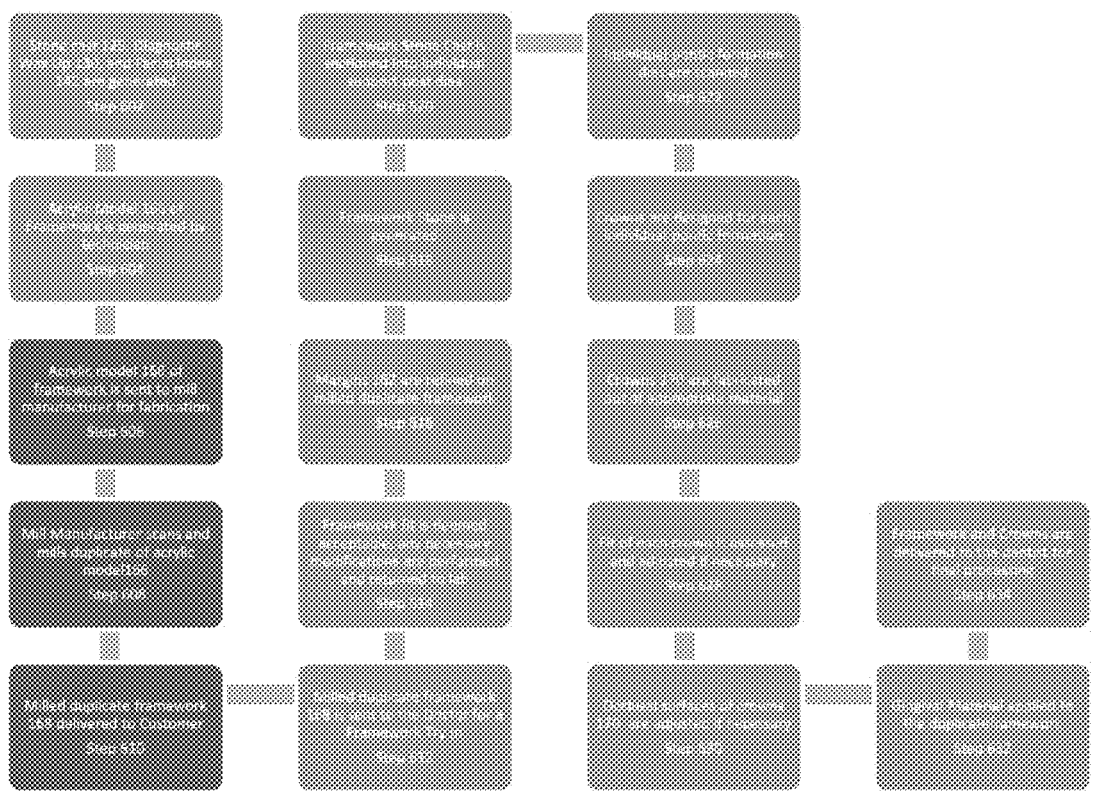
FIG. 11A is a flow chart demonstrating the steps necessary for fabricating a framework to receive individual crowns through a "copymill" procedure.

The steps associated with the traditional "individual crown copymill" process are outline in flowchart 600 of FIG. 11A. As noted in STEP 604 of Flowchart 600, the Dentist or technician will begin to fabricate an acrylic model of the framework that will be duplicated in a material such as titanium, cobalt chrome, zirconia, or any other appropriate dental material. The first step in this process is creating a facial or putty index of the diagnostic wax-up 130 while positioned on stone cast 125, which captures the facial/buccal contours of the denture teeth 132 including their height and angulation and the soft tissue contours of the diagnostic wax up. FIGS. 8 and 9A-B illustrate the process of creating the facial index. FIG. 8 shows the facial index 142 as created using stone cast 125 and diagnostic wax up 130. This facial index 142 is created by wrapping a silicone putty material 144 commonly used in the dental industry around the facial/buccal aspect of the diagnostic wax up 130 while it is properly positioned on stone cast 125. The facial index will engage a significant area of the stone cast 125 that is not covered by diagnostic wax up 130. The facial index 142 will have a unique stone mating area 145 that will allow for the facial index to be properly positioned back to stone cast 125 without the aid of diagnostic wax up 130. FIG. 9A is a cross-sectional view through the facial index 142, stone cast 125, and diagnostic wax up 130, demonstrating the capturing of the buccal aspect of denture teeth 132. This cross-section is taken at section line 9-9 in FIG. 8. Once the putty material 144 has set the facial index 142 and diagnostic wax-up 130 can be removed from the stone cast 125. FIG. 9B shows the negative impressions 147 left by the facial/buccal contours of denture teeth 132. The facial index 142 will be placed back onto the stone cast 125 utilizing the unique stone mating areas 145. The dentist or technician will utilize facial index 142 as a guide to begin building the acrylic model of the intended framework. As demonstrated in FIG. 10A, wax copings or fittings 152A-F will be attached to the mating surface of the analogs 124 and begin stacking acrylic material 160 on top of them to begin forming the design. The acrylic material 160 can be a light cured or cold cured resin commonly used in dentistry. It can also be appreciated that materials other than acrylic such as wax can be used in creating the design of the framework by the dentist or technician. Frequently the dentist of technician will utilize a hand piece and bur to reduce and refine the contour of the acrylic material 160 in order to create the necessary margins 162 and support posts 164 that the individual crowns will be intended to mate to on the framework. As shown in FIG. 10B, the support posts 164 will be attached to one another by bridging structure 154 that will run between fittings 152. The inventor is using the term support posts as a descriptive term in this application, but others may refer to this framework feature as a pontic, abutment, prep tooth form or framework abutment. The support posts 164 will be designed in such a way as to support a crown that will be designed to mate to the margin 162 as designed into the framework. Depending upon the tooth type, the design of the support post 164 will be adapted per the dentist or technician to support the crown against the expected occlusal forces of the patient.

Once the acrylic model 166 of the framework is deemed acceptable the dentist or technician will send the acrylic model 166 and stone cast 125 to a laboratory or framework supplier to have the acrylic model duplicated in the material of their choosing. These STEPS 606, 608, and 660 are noted in Flowchart 600 shown in FIG. 11A. The laboratory or framework supplier will scan the stone cast 125 to determine the orientation and location of the mating surfaces of analogs 124 and scan the acrylic model 166 to capture the contours designed by the dentist or the technician. Once an appropriate rendering of the acrylic model 166 has been generated, a tool path will be generated for fabricating the framework out of the appropriate material. The laboratory or framework supplier can use a number of manufacturing methods, such as milling, 3D printing, laser sintering, ceramic pressing, EDM (electric discharge manufacturing), etc . . . , in a multitude of materials, such as titanium, zirconia, cobalt chrome, semi-precious metals, etc. . . . to fabricate the resulting framework. It can also be appreciated that the dentist or technician may also possess the scanning and/or fabrication equipment necessary to perform these tasks or a portion of these tasks internally within their own facility.

Once the acrylic model 166 of the framework has been duplicated in the appropriate material the duplicate framework 168 and stone cast 125 are returned to the dentist or technician. As noted in STEPS 662 and 664, the duplicate framework 168 is placed in the patient's mouth onto anchors 104 and reviewed for fit and to ensure the duplicate framework 168 has the appropriate contours necessary for the final prosthesis. The dentist and technician may choose to alter some of the contours of the framework to better accommodate the necessary function, aesthetics and phonetics of the patient. These alterations can vary from reducing the height of the support posts 164 or reducing a facial/buccal/lingual contour of bridging structure 154 to reduce the potential of the prosthesis from extending into the cheek or tongue. Some dentists and technicians may elect to skip these steps.

As noted in STEPS 666-630, the dentist or technician can begin fabricating the crowns. The process outlined here in is in utilization of dental scanning unit commonly found in the market place. More detailed information regarding this process can be found in patent application Ser. No. 11/576,450. The following information will only briefly cover the necessary steps associated with this process to provide a general understanding and should not be considered a detailed outline for the different scan/design systems currently available in the dental market. It can also be appreciated that the crowns can be fabricated by alternative means such as a more traditional waxing and casting method. This enclosed process should only be considered as exemplary. In STEP 666, the dentist or technician will refine the margins 162 of the framework where the crowns will mate. Many times the manufacturing process used in creating the duplicate framework can leave tool marks or additional material in these small areas due to limitations of tool size, access, or limitations of the manufacturing process itself. Using a hand piece and bur, the dentist or technician will remove any material left by the manufacturing process to create a clear and uniform margin 162 around the support post 164. Once the margins have been refined appropriately, the framework while positioned on stone cast 125 will be impressed utilizing an impression material 122 and a second framework stone will be created with dental stone material 126. These processes are noted as STEPS 668 and 620 in Flowchart 600. The dentist or technician will section the stone support posts from one another by splitting the framework stone into multiple individual dies. The individual support post dies will be separately scanned to accurately capture the margin where the crown will mate to the framework. The support post dies will be scanned together and a stone cast of the opposing arch will be scanned in an appropriate orientation relative to the support post formations. These scan sets will be appropriately aligned relative to one another. A crown for each support post will be designed virtually. This process can take considerable time for the dentist or technician in creating the individual support post dies, scanning each one, and then in turn designing an appropriate crown. Once the virtual models of the crowns are complete, the models are typically loaded into a mill where the crowns are manufactured out of an appropriate material such as zirconia, titanium, semi-precious metal, lithium disilicate, plastic, PMMA, acrylic, resin ceramic (Lava-Ultimate, Vita-Enamic), etc. . . . . The crowns can also be manufactured by means of additional manufacturing processes, such as 3D printing, laser sintering, ceramic pressing, EDM, etc. . . . . Once all of the crowns 170 have been fabricated their fit is assessed against the margin 162 and support posts 164 of duplicate framework 168, as noted in STEP 628. Many times the technician or dentists have to reduce or modify the contours of the framework or crown in order to achieve the appropriate fit. If the fit is deemed unacceptable, the dentist or technician may need to attempt at refabricating the crown, which may result in creating a new impression of the framework and repeating the tasks associated with fabricating the necessary crowns, STEPS 668-628. These errors and reworks can be costly, time consuming and prevent the final prosthesis from being completed in a timely manner. When all of the crowns have been deemed to fit appropriately to the duplicate framework 168, the dentist or technician will check the occlusal contacts of the crowns against the opposing dentition and modify utilizing a hand piece and bur to reduce the occlusal contours and provide the appropriate level of contact with the opposing arch. A gingival mask can be applied to the framework, which can be performed in several ways either by processing pink acrylic, stacking composite materials, or applying porcelain onto the duplicate framework 168. These processes are commonly known in the dental industry and will not be covered in great detail here in this application. Finally the dentist is ready to deliver the duplicate framework with the gingival mask and cement the crowns 170 onto the framework in the patient's mouth.

Figure 11B:
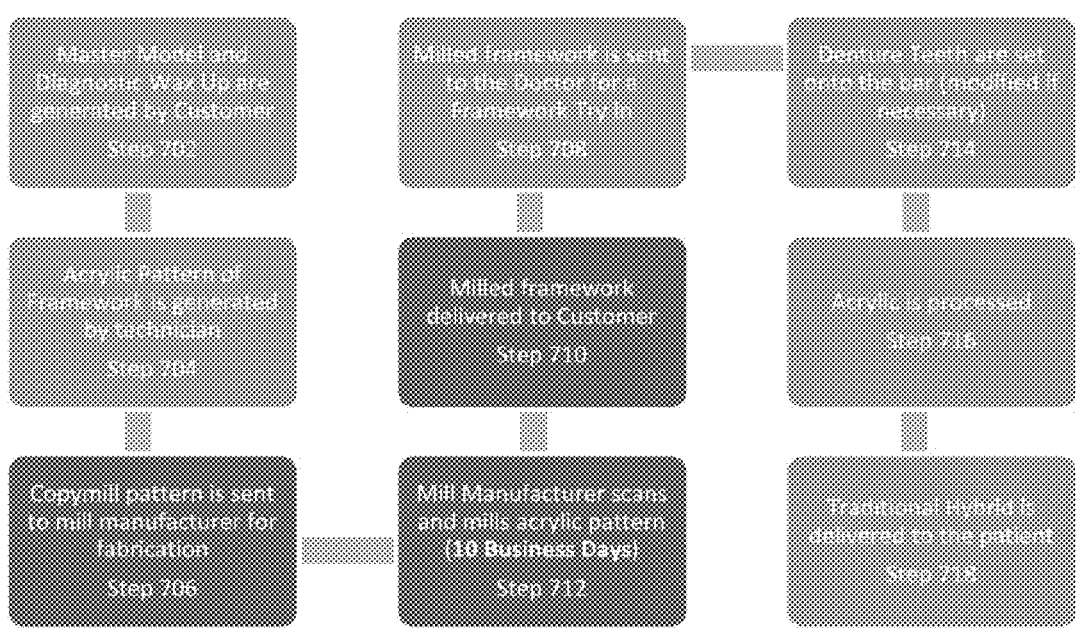
FIG. 11B is a flow chart demonstrating the steps necessary for fabricating a framework through a "copymill" procedure for a traditional acrylic processed hybrid utilizing individual denture teeth.

If the framework design was indicated for a traditional hybrid design, the technician will not perform all the STEPS outlined in FIG. 11A. FIG. 11B provides a list of reduced steps that excludes the requirements for designing and fabricating the individual crowns. Also the dentist or technician will not be required to include or refine the margins or the support posts as previously discussed. Once the framework has been fabricated, the dentist or technician will begin to set the denture teeth to the framework as noted in STEP 714. Many times the underside of the denture teeth have to be reduced or modified in order to be correctly positioned relative to the bar and the opposing dentition and in order to create room for the acrylic that will be processed. There may also be times when the fabricated framework is reduced rather than the denture tooth. The dentist and technician have to be careful in performing these modifications. If the lower acrylic portion of the denture teeth are reduced significantly, the processed acrylic will not be able to bond appropriately to the denture teeth and the denture teeth can break free from the acrylic when occlusal loads are distributed onto the prosthesis. If the framework is reduced significantly, the mechanical strength of the framework can be compromised and the framework will begin to flex during occlusal loading potentially leading to the framework and/or acrylic breaking. Once the Denture teeth have been properly set, the dentist or technician will process the acrylic through a commonly known method (injection, packing, pour, VLC—visible light cured, heat cured, cold cure). The dentist or technician will refine and polish the processed acrylic and deliver the finished restoration to the patient.

In addition to duplicating an acrylic model 166 of the framework, the dentist or technician can utilize a process as outlined in U.S. Pat. No. 8,100,692, where the framework is digitally design on the basis on the soft tissue contours of stone cast 125 and position of the denture teeth and gingiva contours of diagnostic wax up 130. This process alleviates the need for an acrylic model and provides for an improved design in knowing the position of the buccal and lingual boundaries of the prosthesis. However this process cannot guarantee that the denture teeth or framework will not need to be modified prior to processing the acrylic or prevent the potential breakages noted above.

Figure 12A:
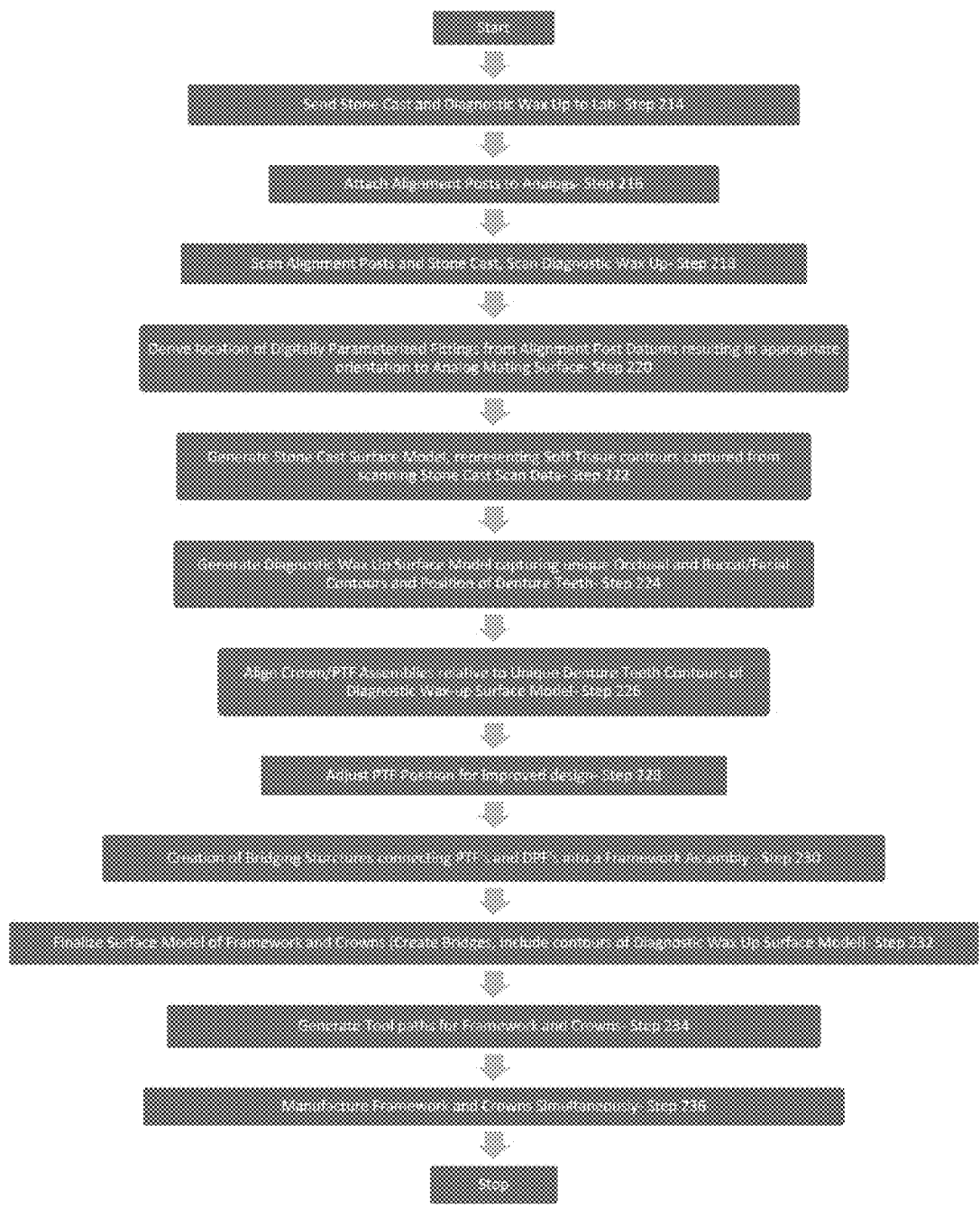
FIG. 12A is a flow chart demonstrating the steps for the process in designing and fabricating a dental prosthesis composing of an implant framework and series of crowns/bridges per patent application Ser. No. 14/272,566.

In creating a dental prosthesis consisting of an implant framework supporting a series of crowns/bridges as outlined in application Ser. No. 14/272,566, the dentist and/or technician will create a stone cast 125 and diagnostic wax-up 130 as previously discussed. It is from these elements, where the invented process will allow for the simultaneous design and fabrication of the crowns and framework. First a digital scan of the stone cast 125 utilizing the alignment posts 156 attached to the analogs 124 as detailed in application Ser. No. 11/875,826, is conducted. This process will determine the exact location of the critical mating geometries and their correlation relative to one another as well as relative to the soft tissue contours captured in the stone cast. As demonstrated in FIG. 12A, in step 214 of the process, the dentist sends the stone cast 125 and diagnostic wax up 130 to the laboratory. In step 216, the laboratory inserts alignment posts 156 into the analogs 124 embedded in the stone cast 125. These alignment posts 156 are configured to engage the mating surfaces of analogs 124 and hold the alignment posts coaxial with the longitudinal axis of analogs 124. They may have differently shaped flat, frusto-conical and cylindrical surfaces configured to engage with the mating surfaces of analogs 124. The alignment posts 156 used in this process have two spherical surfaces comprising centers coaxial with analog 124. These alignment posts need not have spherical surface portions, but may have any predetermined geometric shape as deemed suited by the user. This process also encloses the use of a single gauge; however it can be appreciated that a series of gauges could be used instead of a single embodiment to achieve the same result.

The mating surfaces on the alignment posts and the mating surfaces on the analogs 124 inter engage to cause the alignment posts 156 to be aligned coaxial with analogs 124. The alignment posts 156 cover the free ends of the analogs 124 exposed in stone cast 125.

In step 218, once the alignment posts 156 have been attached to the analogs 124, the scanner 182 is configured to scan the alignment posts and the soft tissue replica of the patient's mouth formed in the surface of the stone cast 125, and the alignment posts 156. The surfaces of stone cast 125 that are scanned by scanner 182 include the surfaces of the stone cast that replicate the mucosal tissue in the patient's mouth. Scanner 182 stores in the memory of computer 186 a first point cloud dataset of the stone cast 125 with alignment posts 156 attached. In step 218, scanner 182 also scans the surface of diagnostic wax-up 130 and the surface of stone cast 125 (preferably when they are assembled) and saves a second point cloud dataset collectively representing the scanned surface of the diagnostic wax-up 130 and stone cast 125. Alternatively, the operator can scan the diagnostic wax-up 130 separately from the stone cast and later register the point cloud dataset of the stone cast 125 and the diagnostic wax-up 130.

If the diagnostic wax up 130 is scanned on the stone cast 125, the scan preferably includes data points taken from all the exposed external surfaces of the diagnostic wax-up 130 (i.e. the outwardly facing surfaces that model the gum and the teeth) as well as surfaces of the stone cast 125 adjacent to the diagnostic wax-up 130. The surfaces of the stone cast 125 adjacent to the diagnostic wax-up that are scanned in the second point cloud dataset are also preferably scanned in the first point cloud dataset and thus there is some overlap in surface contours in both the first and the second point cloud datasets—both datasets include data points scanned from the same surfaces of stone cast 125. This permits later registration of the first and second point cloud datasets.

If the diagnostic wax-up 130 is scanned when it is separate from the stone cast 125, it is preferably scanned so that the second point cloud dataset includes data points taken from all the exposed external surfaces of the diagnostic wax-up 130 (i.e. the outwardly facing surfaces that model the gum and the teeth) as well as surfaces of the diagnostic wax-up 130 that would abut stone cast 125 if the diagnostic wax-up 130 was mounted on the stone cast. Since the diagnostic wax-up 130 was formed by molding a plastic (or wax or acrylic) material to the surface of the stone cast 125, the scanned surface contour of the diagnostic wax-up 130 that abut the stone cast are a mirror image of surface contours of the stone cast 125.

In the preferred embodiment these abutting stone cast 125 surfaces were scanned previously and are a part of the first point cloud dataset. Thus, the first and second point cloud datasets include a subset of data points taken from mirror image surface contours—surface contours common to both the first and second point cloud datasets—common to the diagnostic wax-up 130 and to the stone cast 125. This permits later registration of the first and second point cloud datasets.

In step 220, computer 186 determines the location and orientation of the alignment posts as they are attached to analogs 124 in the stone cast 125. Computer 186 sequentially selects a digital parameterized fitting 152" from its internal library and aligns the mating surface (or surfaces) and axis of the selected digital parameterized fitting 152" with the surface (or surfaces) and axis of one of the analogs based upon datums derived from the alignment posts 156. Computer 186 repeats this process for each additional analog 124 whose location and orientation were determined in step 220, until it has built up an initial surface model of dental framework 324.

In step 222, a surface model of the unique contours of stone cast 125 is created which is a representation of the soft tissue contours in the patient's mouth. The stone cast surface model 320 will provide a lower limit to which the framework can be designed to.

In step 224, a surface model of the unique contours of diagnostic wax up 130 is created which is a representation of the proposed prosthesis for the patient. The diagnostic wax-up surface model 322 contains the unique buccal/facial and occlusal contours of the denture teeth 132. The diagnostic wax-up surface model 322 will provide the necessary information regarding the orientation of the individual denture teeth 132 as they are positioned relative to one another within diagnostic wax-up 130. The diagnostic wax up surface model will also capture any unique gingiva contours as designed by the dentist or technician.

The surface models 320 and 322 can be the raw point clouds derived from the scan data of the stone cast 125 and diagnostic wax-up 130 or can be a sheet body, where a surface has been wrapped across the raw point clouds. These models can also be closed surface models, allowing for Boolean Unite and Subtract Operations to be performed utilizing these models or other CAD bodies.

The two sets of scan data and resulting surface models of the stone cast 125 and diagnostic wax-up 130 provide all of the necessary data for determining the position of the denture teeth 132 in diagnostic wax-up 130 relative to the implants and abutments and the soft tissue contours of stone cast 125 as well as defining the boundaries or limits in which the framework should be designed within. The scan data of the diagnostic wax up 130 will provide all of the necessary positional information for determining the correct orientation of the crowns and related support posts (The term prep tooth forms or PTF can be used in place of the term support posts. Both prep tooth forms (PTF) and support posts are descriptive of the portion of the framework that will mate with and support the crown.).

Figure 13:
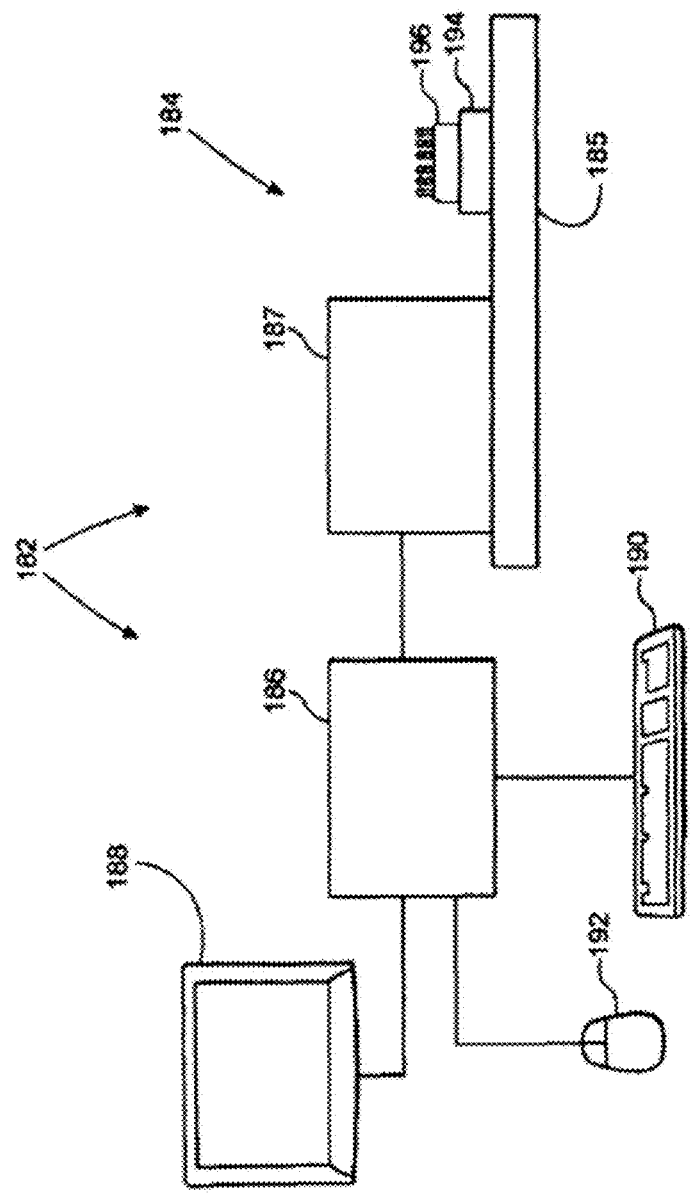
FIG. 13 is a schematic diagram of the scanner and the wax-up framework and alignment posts that it is scanning.
Figure 14A:
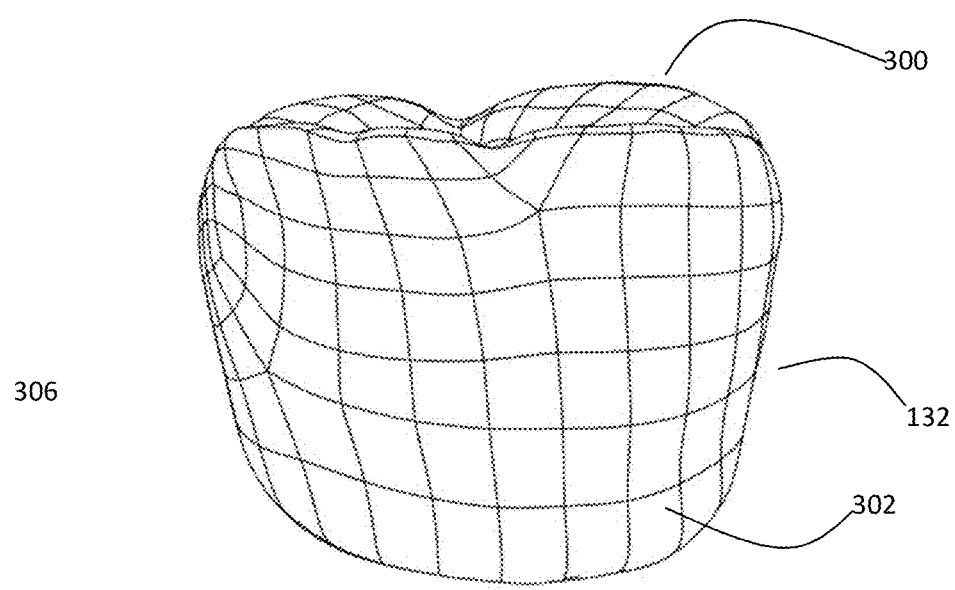
FIG. 14A is a front view of the graphical representation of the surface model scanned from the denture tooth.
Figure 14B:
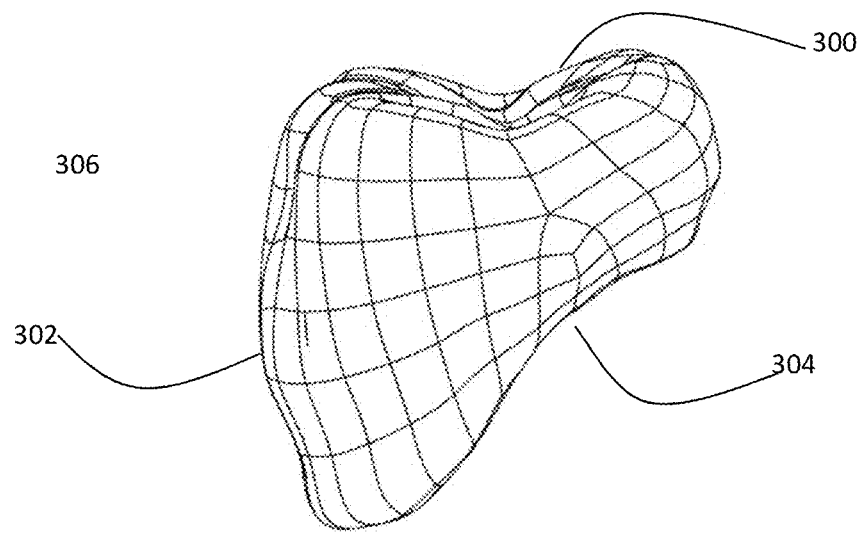
FIG. 14B is a side view of the graphical representation of the surface model scanned from the denture tooth.
Figure 15A:
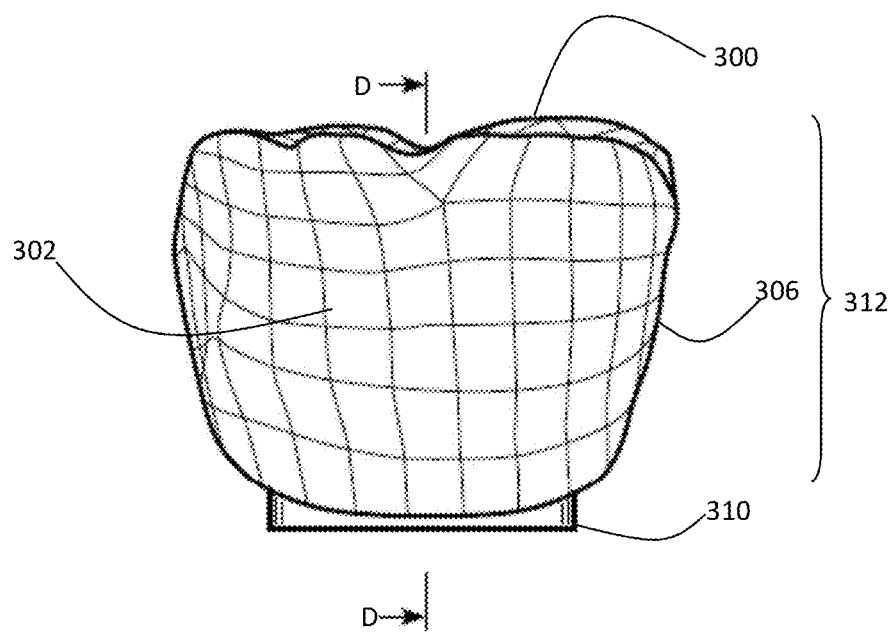
FIG. 15A is a front view of the graphical representation of the crown and support post/prep tooth form models.
Figure 15B:
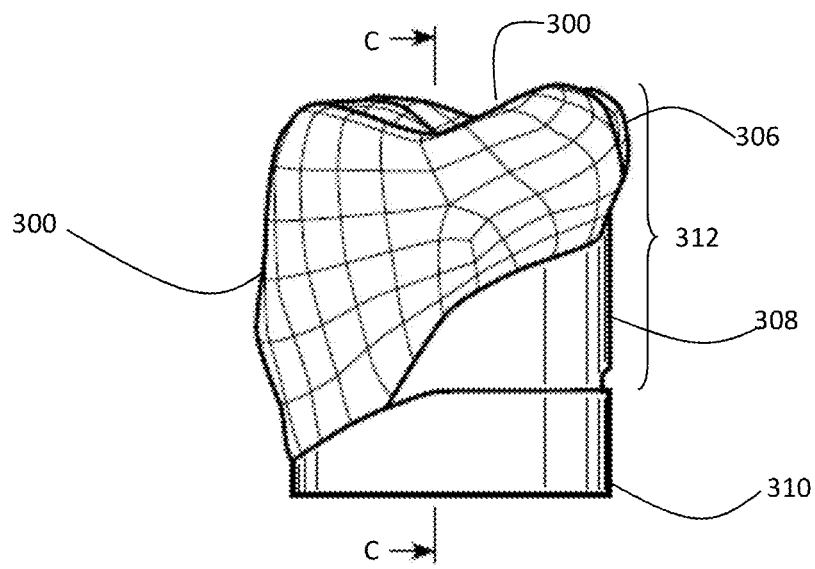
FIG. 15B is a side view of the graphical representation of the crown and support post/prep tooth form models.
Figure 15C:
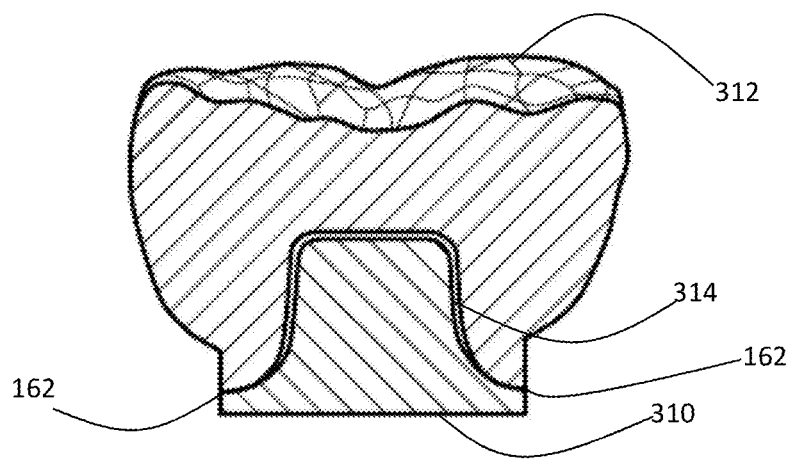
FIG. 15C is a cross sectional view of the crown and support post/prep tooth form models of FIG. 15B taken at section line C-C in FIG. 15A.
Figure 15D:
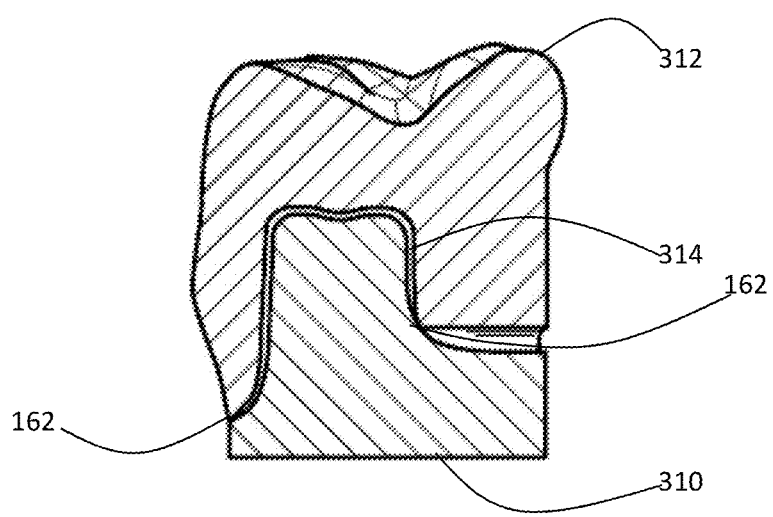
FIG. 15D is a cross sectional view of the crown and support post/prep tooth form models of FIG. 15A taken at section line D-D in FIG. 15B.

The framework is created through a novel concept in utilizing a library of crown models and prep tooth forms (support posts). The crown models are based upon known dimensions of standard tooth sizes. Many of the current dental design software systems, such as Procera, 3Shape, or Dental Wings, have a library of digital crown or tooth files based upon these standard dimensions. Stock Denture Teeth are also constructed on the basis of the standard tooth size and are commonly used in the construction of dentures, over-dentures, and fixed hybrid restorations for treatment of the edentulous patient. Also some of the previously mentioned software systems include models of the denture teeth in their library. As discussed previously, these denture teeth 132 are commonly used in the dental market and consist of known dimensions that have been standardized for mass production. By utilizing a non-contact or touch probe scanner similar to the one described in FIG. 13, an operator can capture the unique contours of the commonly available denture teeth 132 that are used by the dentist or technician in creating the diagnostic wax up 130. FIGS. 14A-B show a model of the reverse engineered denture tooth and shows the unique occlusal contours 300 and buccal/facial contours 302 captured during the scanning process. The scanning process will also capture the intaglio surface 304 or underside of the denture tooth, which will enable for the creation of a denture tooth model 306. On the basis of the denture tooth model 306 and occlusal contours 300 and buccal contours 302, a PTF 310 can be designed to optimally support a crown that has the same or similar contours as the denture tooth. The Prep Tooth Form or PTF 310 can be designed to accommodate an appropriate wall thickness of the crown and provide an ideal margin 162 where the crown will mate with the framework. The crown model 312 consists mostly of the contours of the reverse engineered denture tooth 132 captured in denture tooth model 306, but additional features or material can be added to the crown model in generating an ideal mating surface that will interface with the PTF or provide an ease in manufacturing. The added lingual crown material 308 as shown in FIGS. 15A and 15B has been included into the design to create a more planar mating surface or margin 162 between the crown model 312 and PTF 310. However it can be appreciated that the mating surface or margin 162 can be non-planar and provide a margin 162 that is more in line with one that the dentist or technician would find for a prepped tooth or custom abutment. The lingual crown material 308 can be designed to aid during the gingival masking process. In this example, straight parallel walls have been included into the design to improve the retention of the crowns after acrylic processing. An appropriate cement gap 314 also has to be designed into the crown model 312 to provide the necessary space for dental cement that will allow for the crown to be fixated to the framework. The cement gap 314 will terminate at margin 162, where the crown and framework will ultimately mate.

The crown model 312 can be designed in a parametric or non-parametric CAD body. In the non-parametric form, the crown model is a rigid duplicate of the denture tooth model 306. This non-parametric model does not provide the CAD Operator with an ability to easily modify the surface or contours of the crown model 312. For a non-parametric CAD body, the operator will have to use Boolean and Trim functions to add or subtract additional features in order to change the occlusal contours 300 and buccal contours 302 of the crown model 312. In comparison the parametric CAD body can be constructed of a series of splines and sheets, possessing data points or poles, allowing for the CAD Operator to modify or alter the surface of the crown model 312. The parametric CAD body allows for easy manipulation of the crown model surface to accommodate any design requirements required by the dentist. One example of manipulating the crown model surface would be modifying the occlusal contours of the crown. The dentist or technician may choose to lower or heighten all or portions of the occlusal surface to provide an ideal occlusal relationship with the opposing arch. Another example would be modifying the mesial/distal side contours in order to increase or decrease the mesial/distal contacts between the crowns.

FIGS. 15A-F depict an exemplary crown model and PTF. FIGS. 15A-F depict a molar crown model 312 and PTF 310. For demonstration purposes this application will only show the design of a crown model and PTF for a molar tooth. It can be appreciated that the PTF can be designed to properly accommodate any size tooth, such as an incisor, cuspid, or premolar. It can also be appreciated that any denture tooth system can be incorporated though the disclosed process. There are also available libraries of stock crown CAD files, in many of the dental design systems that can be incorporated and utilized in addition to reverse engineering the stock denture teeth. The PTF 310 has been designed to properly support the cusp structure of the reverse engineered denture tooth and the designed crown model 312. The design of the PTF 310 can also be modified in any way deemed appropriate by the designer to meet the requests of the customer. The height and width of the PTF can be altered to better deal with the restorative space presented with the case. The enclosed PTF design has a much more flat and planar design associated with the margin 162. Other designs may utilize a much more natural root form margin that comes up higher in the mesial/distal aspects of the crown and lower in both the lingual/buccal aspects.

Figure 15E:
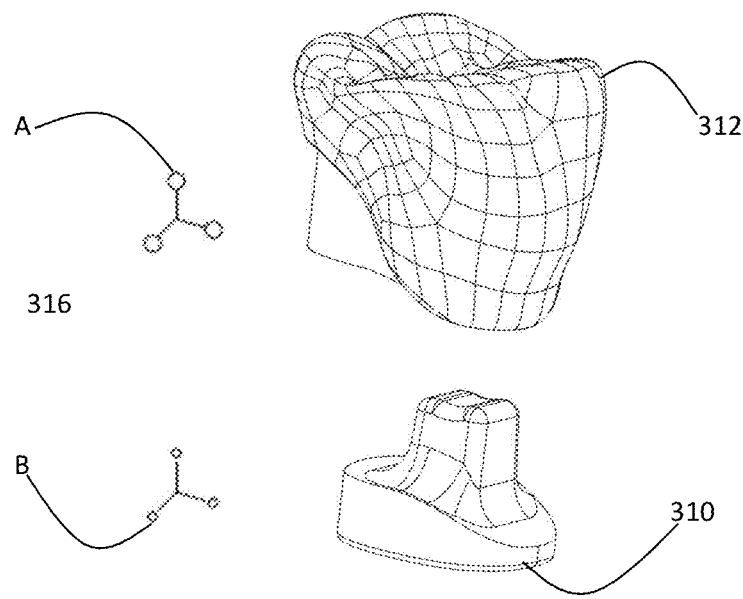
FIG. 15E is a perspective view of the crown and support post/prep tooth form models demonstrating their alignment separate from one another possessing independent coordinate systems.
Figure 15F:
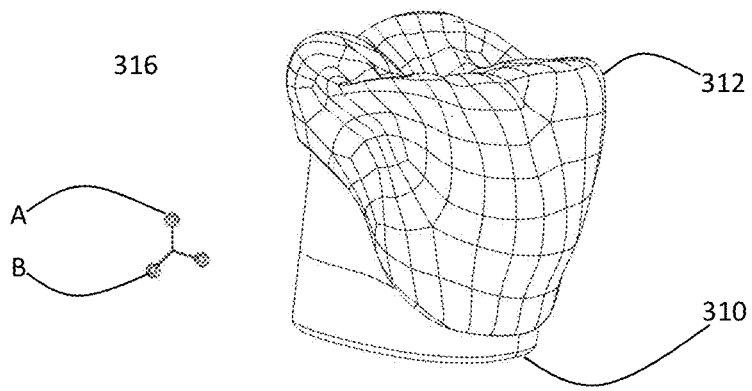
FIG. 15F is a perspective view of the crown and support post/prep tooth form models aligned correctly relative to one another and showing their individual coordinate systems aligned correctly to one another.
Figure 15G:
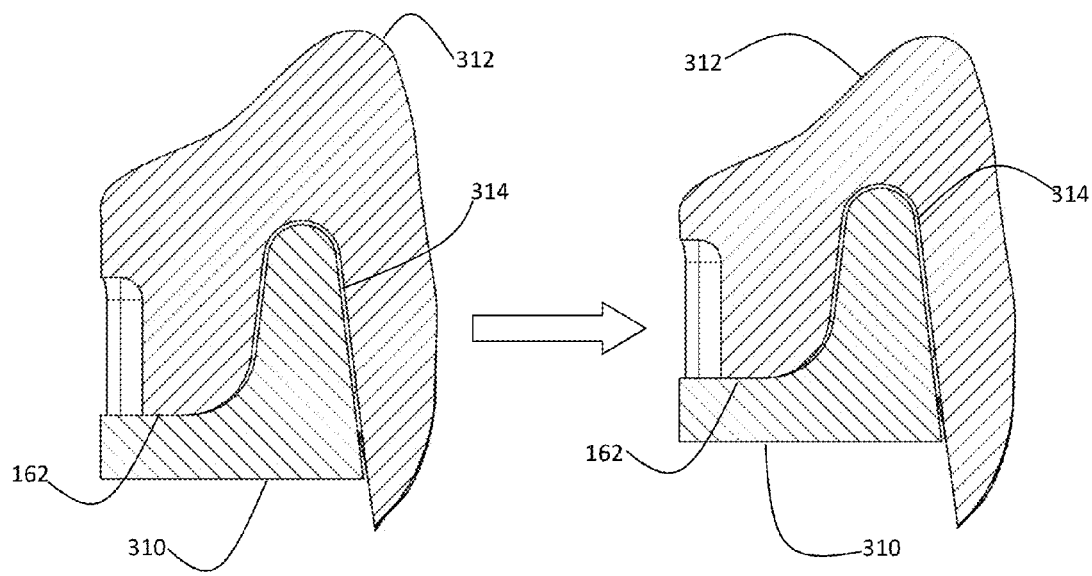
FIG. 15G is a cross-sectional view of a crown and support post/prep tooth form model and demonstrates the feature dependency created between the crown and support post/prep tooth form models, where the cement gap and margin have been automatically updated based upon the support post/prep tooth form being positioned higher.
Figure 15H:
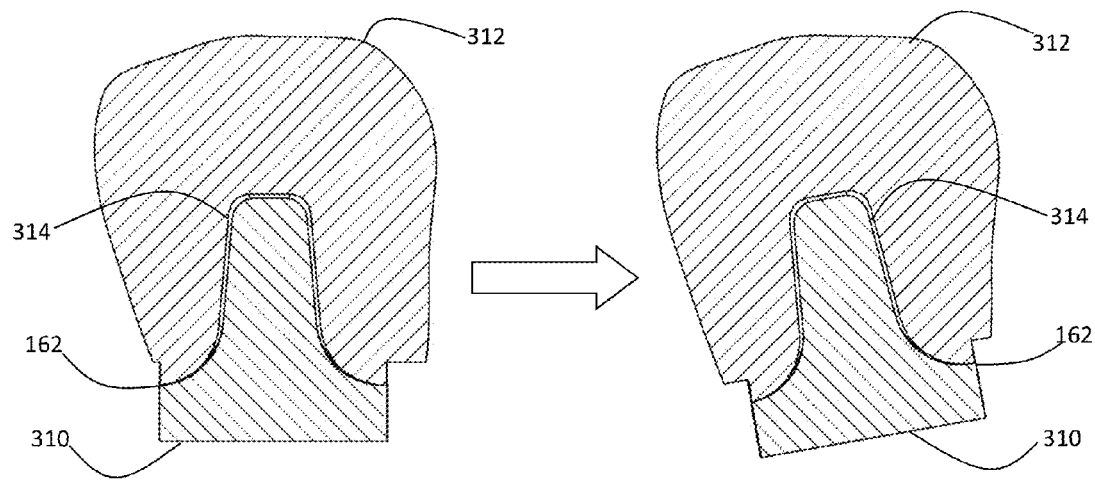
FIG. 15H is a cross-sectional view of a crown and support post/prep tooth form model and demonstrates the feature dependency created between the crown and support post/prep tooth form models, where the cement gap and margin have been automatically updated based upon the support post/prep tooth form being angulated to a new orientation.

As demonstrated in FIGS. 15E-F the crown model and PTF can be combined into assembly 316 and share the exact coordinate system, allowing for them to be aligned relative to one another in an ideal fashion. Assembly 316 allows for the crown model 312 and PTF 310 to be readily imported and remain properly aligned relative to one another. However it can also be appreciated that the crown model 312 and PTF 310 can be imported separately depending upon the CAD system or processes being implemented by the Operator. One example of importing PTF's 310 without the crown files would be if the dentist or technician is planning on creating custom crowns for the final restoration. In this instance the utilization of the crown files may be completely unnecessary and the operator can position PTF 310 in the ideal position to support the crown. This exemplary process would also allow the technician to utilize one of the other dental design software packages previously mentioned to design and fabricate the crowns, in a similar fashion as through the "copymill" process.

FIGS. 15 A-D show in closer detail crown model 312 aligned appropriately to PTF 310. As depicted in the figures the PTF 310 expands substantially to support the crown model 312 in the mesial distal aspect FIG. 15 A and the lingual facial aspect FIG. 15 B. FIGS. 15 C and D are cross-sectional views of the crown model 312 and PTF 310 showing the cement gap 314 and margin 162 where the crown intimately mates with the PTF. The cement gap 314 and margin 162 can be adjusted by the designer to meet the customer requirements or to better suit the preferred manufacturing process. FIGS. 15 A-F show the ideal orientation of the crown model and PTF. However there are instances when this orientation may not be ideal due a design requirement for a particular case. The crown model and PTF can have a series of dependent features that when a change in the feature of one body is performed, the second dependent body will automatically update based upon this change. One example would be repositioning the height of the PTF. As demonstrated in FIG. 15 G, when the PTF is positioned higher relative to the crown model 312, the cement gap 314 and margin 162 will automatically update to accommodate for this new position.

The crown model 312 and PTF 310 can also be allowed to be positioned in different orientations relative to one another and similarly update on these new positions. Another example as demonstrated in FIG. 15 H would be repositioning the angle of the PTF due to an issue of path of insertion or tool access for manufacturing. As shown in FIG. 15 H, when the PTF is aligned to the new position not only does the cement gap 314 update, but also margin 162 will update to this new alignment. This dependency provides the ability for the designer to make simple modifications in a timely fashion when designing the framework in accommodating a design request for a customer or allowing for an ease in manufacturing.

The crown/PTF assembly 316 can possess additional sub features in addition to the full contour crown surface. The crown model can have subtract features which will provide the technician and dentist with a standard coping or cutback coping that would be ideal in stacking porcelain. The standard coping or cutback coping can be included through the use of a Boolean Subtract Feature or as a separate CAD body within the Crown/PTF assembly 316. The inclusion of these features provides a broad spectrum of restorative elements for the dentist or technician to choose from.

Figure 16A:
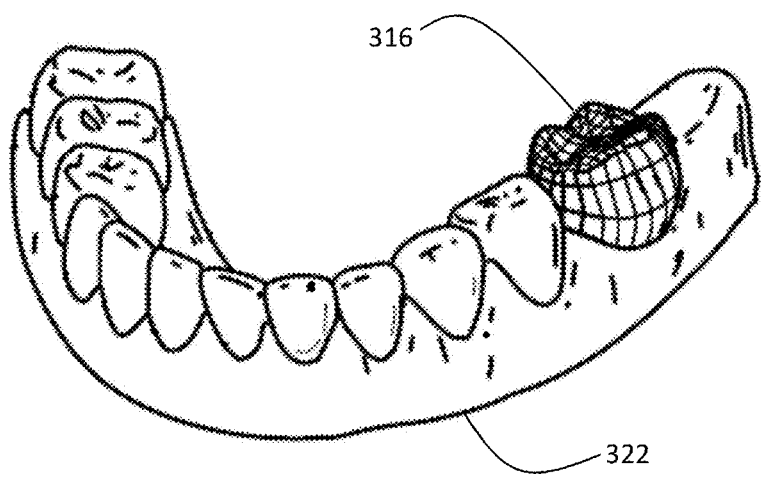
FIG. 16A is a graphical representation of diagnostic wax up surface model with one of the crown and support post/prep tooth form assemblies appropriately aligned.
Figure 16B:
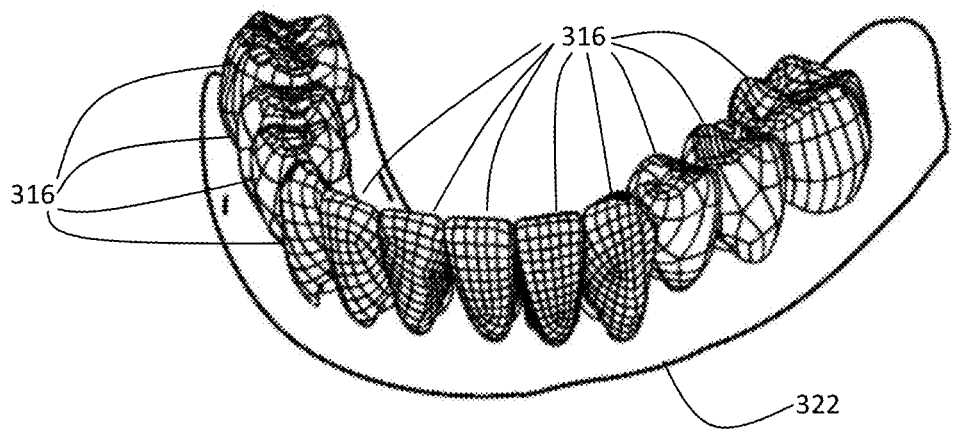
FIG. 16B is a graphical representation of diagnostic wax up surface model with all of the crown and support post/prep tooth form models appropriately aligned.

In step 226 of FIG. 12, the Crown/PTF assembly 316 is imported and aligned relative to the diagnostic wax-up surface model 322. The crown/PTF assembly 316 will have the same surface contours as one of the denture teeth 132 that was incorporated into diagnostic wax up 130. Utilizing a best fit operation, the crown/PTF assembly 316 will be properly positioned on the basis of the facial/buccal and occlusal contours for the specific denture tooth 132. FIGS. 16 A-B demonstrate this process. In FIG. 16A, a molar crown/PTF assembly 316 is aligned appropriately to diagnostic wax-up surface model 322. In FIG. 16B, the additional crown/PTF assemblies are aligned for the incisors, cuspids, premolars, and remaining molar. This alignment process can be carried out by computer 186 automatically or overseen and performed manually by the operator.

Figure 17:
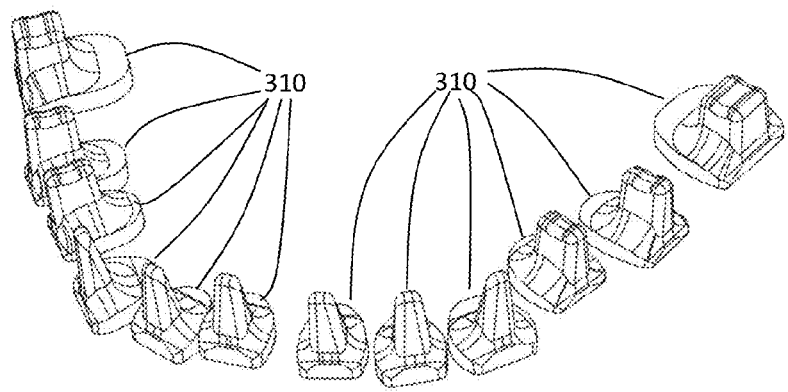
FIG. 17 is a graphical representation of the support posts/prep tooth forms in their appropriate alignment based upon the diagnostic was up surface model.
Figure 18:
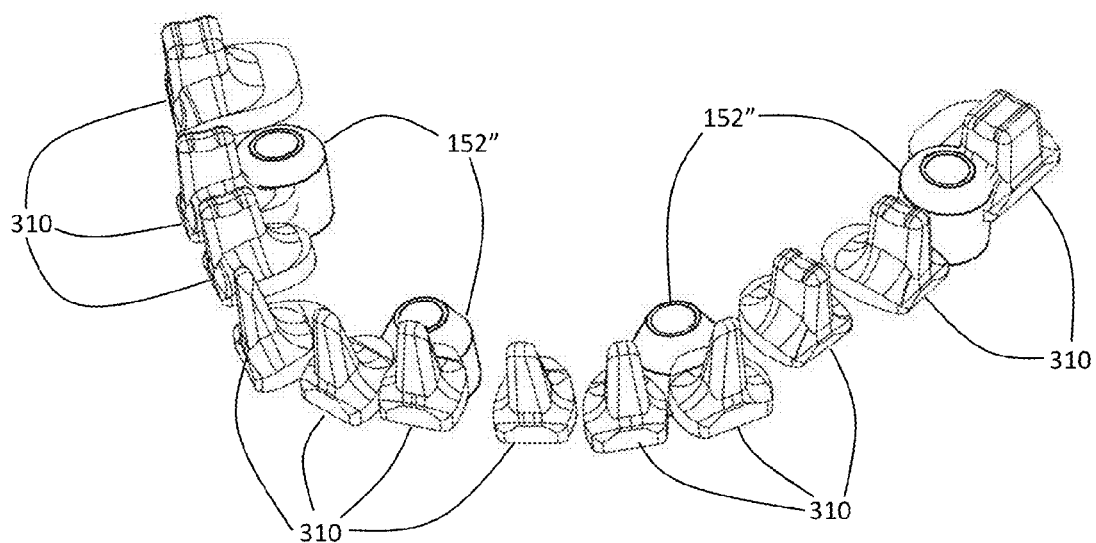
FIG. 18 is a graphical representation of the DPF's and support posts/prep tooth forms appropriately positioned relative to one another in creating the surface model of the framework.
Figure 19A:
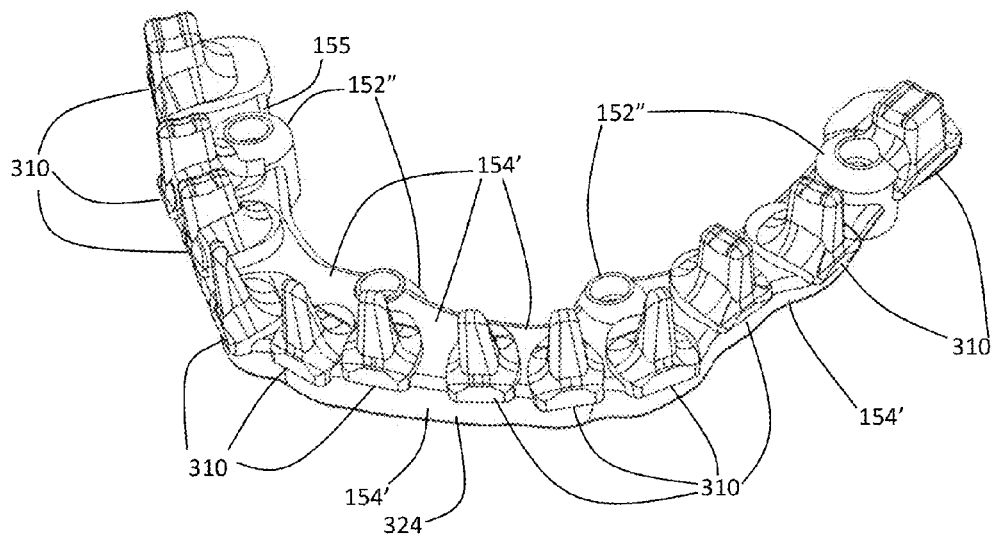
FIG. 19A is a perspective view of the surface model of the framework with the DPF's, support posts/prep tooth forms, and bridging structures appropriately positioned relative to one another.
Figure 19B:
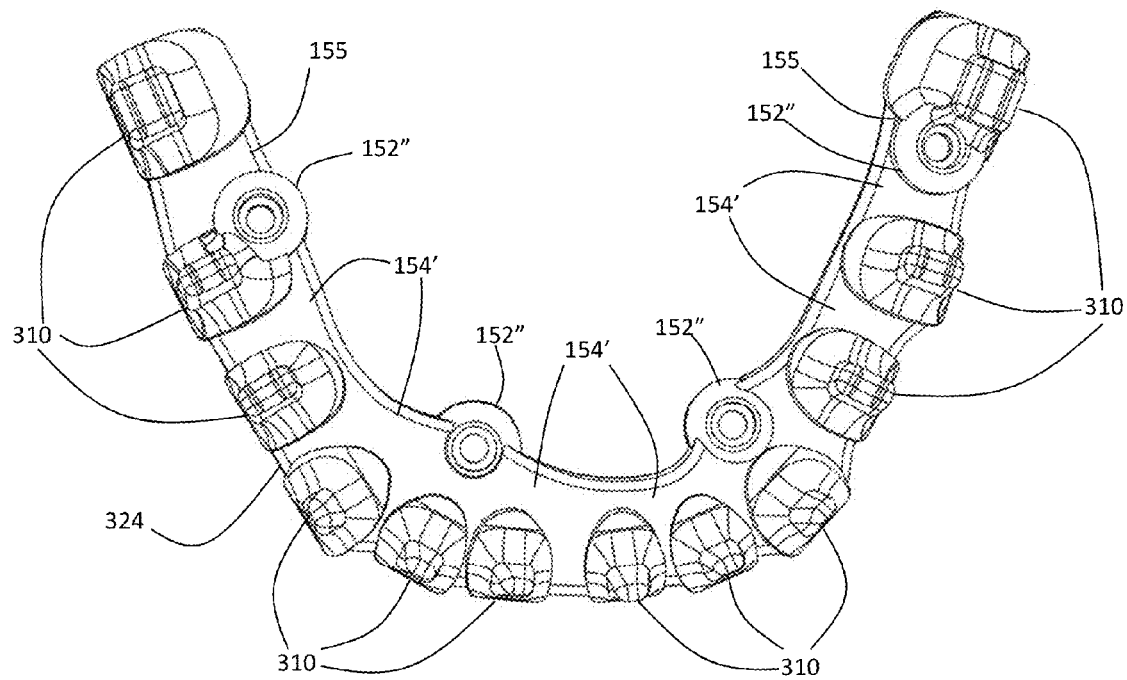
FIG. 19B is a top view of the surface model of the framework with the DPF's, support posts/prep tooth forms, and bridging structures appropriately positioned relative to one another.

In Step 228, the Operator will review and adjust the position of the PTF's 310 to best accommodate the aesthetic and functional demands for the case. As discussed above, this process of moving the PTF's 310 can also accommodate for improved tool access on the basis of the manufacturing method. Once appropriately positioned into the proper orientation, the cement gap 314 and margin 162 will automatically update on the basis of this new position. FIG. 17 shows all of the PTF's 310 in there appropriate position, while the crown models 312 and diagnostic wax-up surface model 322 are hidden. FIG. 18 shows the PTF's 310 and DPF's 152" properly positioned relative to one another. In step 230, the computer 186 is configured to generate a surface model of bridging structure 154' (FIGS. 19 A-B) that will join PTF's 310 and the digital parameterized fittings 152". This includes the computer 186 determining the cross-sectional shape, length and location of the bridging structures as described below. This surface model of this bridging structure 154' extends between and joins PTF's 310 and the digital parameterized fittings 152" and thereby completes the surface model of the dental framework 324. Bridging structure 154' also comprises the portions 155 that extend away from the end digital parameterized fittings 152" and are supported only at one end. One form of the bridging structure is shown in FIGS. 19A-B as a simple elongated member having a predetermined cross section.

To generate bridging structure 154', computer 186 determines the shape, length, and location of the individual portions of the bridging structure to attach PTF's 310 and digital parameterized fittings 152". It is further configured to determine the shape length and location such that the individual portions will not intersect the stone cast surface model 320. Since the surface of the stone cast 125 represents the exposed surfaces (including mucosal tissue) in the patient's mouth, this reduces the likelihood that the physical framework created from the surface model will contact and damage the patient's mucosal tissue. Computer 186 is configured to provide a separation distance between the surface model of the stone cast and the bridging structures. In one arrangement the computer 186 is configured to place the bridging structures a predetermined minimum distance from the surface model of the stone cast. In another arrangement the computer is configured to permit the operator to select a desired minimum distance between the bridging structure and the stone cast surface model 320. In another arrangement, the computer is configured to offer to and/or accept from the operator only a certain range or number of minimum separation distances, such minimum separation distances preferably ranging between 0.1 mm and 5 mm.

Computer 186 is configured to create the bridging structure by providing a pre-designed list of bridging structure forms (e.g., a cylinder, circle, ellipse, square, polygon or other geometric shape) that have been previously stored in the electronic memory of the computer. In one configuration, the computer is configured to automatically select the cross sectional dimensions of each form (diameter, radius, major and minor diameter, height, width, etc.). In another configuration the computer is configured to present the user with a list of pre-set values or defined by the user among which the user can select preferred dimensions. In yet another configuration, the computer is configured to prompt the user to enter specific numeric values for these dimensions. The form of the bridging structures can also be defined by the user.

Computer 186 is configured to determine the proper location of the bridging structure 154' extending between the PTF's 310 and the digital parameterized fittings 152" by locating the beginning and end of each structure according to position information that is derived from the scanned point cloud dataset of the alignment posts. Position of the bridging structure can also be determined by the operator or from the point cloud data set of the stone cast and/or diagnostic wax up.

In another arrangement, the computer 186 is configured to determine the location of the bridging structure 154' extending from each of the PTF's 310 and digital parameterized fittings 152" by locating the beginning and end of each structure according to reference points and axes assigned to the digital parameterized fittings 152" by the computer program from a list of pre-set values or defined by the user. For example, each PTF 310 and digital parameterized fitting 152" which is placed in the model may have only certain types of bridging structures to which they can be connected, and may only connect to those bridging structures at certain locations on the PTF or digital parameterized fitting. This information is stored in the electronic memory of computer 186 in association with each PTF or digital parameterized fitting. When a particular PTF or fitting is inserted into the model, computer 186 is configured to the type and location information associated with the inserted PTF or fitting and locate (or permit the operator to locate) bridging structures of the type and at the locations compatible with those PTF's or fittings. This process can also ensure the bridging structure does not extend into critical mating areas of PTF 310 and digitally parameterized fitting 152" that would affect the potential fit of the crowns or implant/abutments to the framework. In the case of distal extensions 155, computer

186 is configured to cantilever them off the digital parameterized fittings 152" and extend them distally along the arch of the patient's mouth. These distal extensions 155 are preferably 20 mm in overall length or less. They are also selected as described above.

Computer 186 is configured to conduct a mechanical design analysis of the distal extensions 155 that validates shear and bending strength limits for those geometries relative to their chosen material and shapes. Computer 186 is configured to apply the appropriate shear, tensile and compressive stress analysis techniques to the chosen geometries automatically or from a predetermined list of tests chosen by the user. Upon successful analysis of the distal extension designs, the extensions are verified or accepted by the user.

As part of the step of generating the bridging structure 154' computer 186 is configured to determine a location for the bridging structure 154' that will not intersect the diagnostic wax-up surface model 322. This ensures that the bridging structure 154' of the final denture framework will not stick through, but will be disposed within, the body of the diagnostic wax-up 130.

It can be appreciated that all of the disclosed steps being performed by computer 186 can be performed manually by the Operator. The Operator can also determine the use of any number of custom geometries or series of geometries to be used for the bridging structure 154' and distal extensions 155.

Upon completion of the bridging structures 154' and distal extensions 155, the final surface model of the framework 324 is complete. The final surface model of the framework will consist of PTF's 310, DPF's 152", bridging structures 154' and distal extensions 155. FIGS. 19 A-B show the final surface model of the framework 324. Computer 186 will also determine any interference between the crown models 312 and the surface model of the framework 324 that may have been generated during the design process.

Figure 20A:
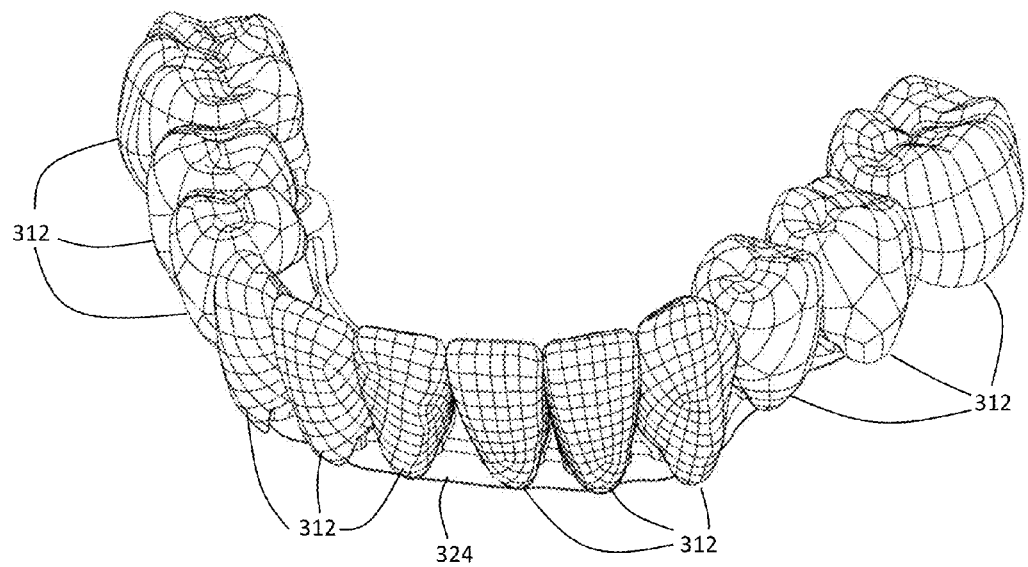
FIG. 20A is a perspective view of the surface model of the framework including DPF's, support posts/prep tooth forms, and bridging structures with the crown models appropriately positioned.
Figure 20B:
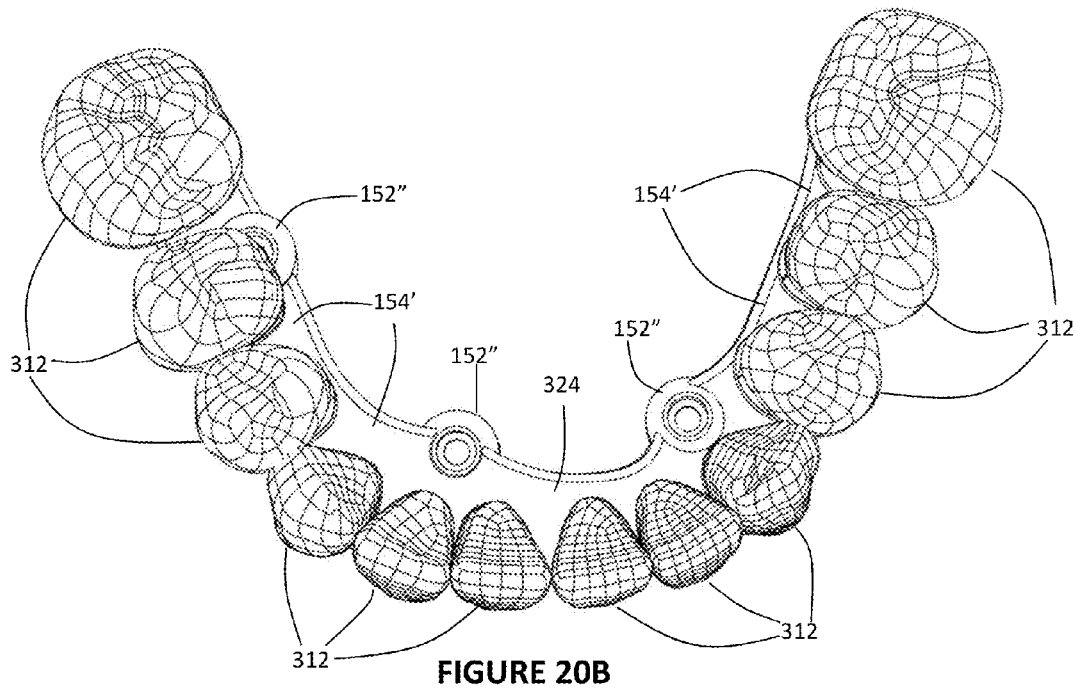
FIG. 20B is a top view of the surface model of the framework including DPF's, support posts/prep tooth forms, and bridging structures with the crown models appropriately positioned.

In STEP 232, computer 186 will finalize the surface model of the framework and crowns by alleviating any interference between these surface models. This process is performed through a Boolean subtraction of the surface model of the framework 324 from crown models 312. FIGS. 20A-B show the crown models 312 and surface model of the framework 324 appropriately positioned relative to one another. At this time the Operator can also choose to include screw access holes into the crown models 312 at the request of the dentist or technician.

Figure 21:
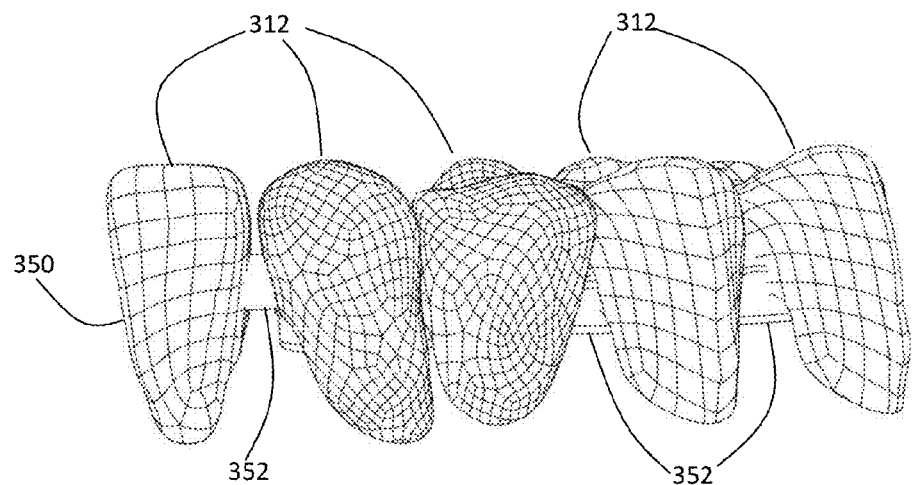
FIG. 21 is a side view of the bridge model.

There also may be times when the dentist or technician may prefer the crown models 312 be adjoined to one another into a bridge due to design limitations associated with the case, such as the position of a screw access hole or limited vertical space, or to meet a personal preference of the dentist. In FIG. 21, crown models 312 have been adjoined to one another in creating bridge model 350. Through a Boolean Union or the addition of other CAD features herein referred to as bridge bodies 352, the crowns 312 can be adjoined to one another as best determined by the Operator and can include all of the crowns or as few as two. In FIG. 21 five crown models have been combined into forming bridge model 350 by means of bridge bodies 352. Bridge bodies 352 can consist of a standardized profile (e.g., a cylinder, circle, ellipse, square, polygon or other geometric shape) or the Operator can custom design an appropriate structure to provide the appropriate mechanical strength to resist against the occlusal forces of the patient's bite. If necessary the Operator can add appropriate features or geometries to ensure the bridging structure will properly mate to the framework and function under the occlusal loads of the patient. At times the creation of bridges or adjoining the crowns may be necessary due to the position of a screw access hole that would significantly reduce the size of a PTF 310 to a point where it would not be able to properly support a crown by itself. In this instance bridging the crown in this area to one or both adjacent crowns would prevent it from becoming damaged or dislodged when placed under occlusal loads by the patient.

Figure 22:
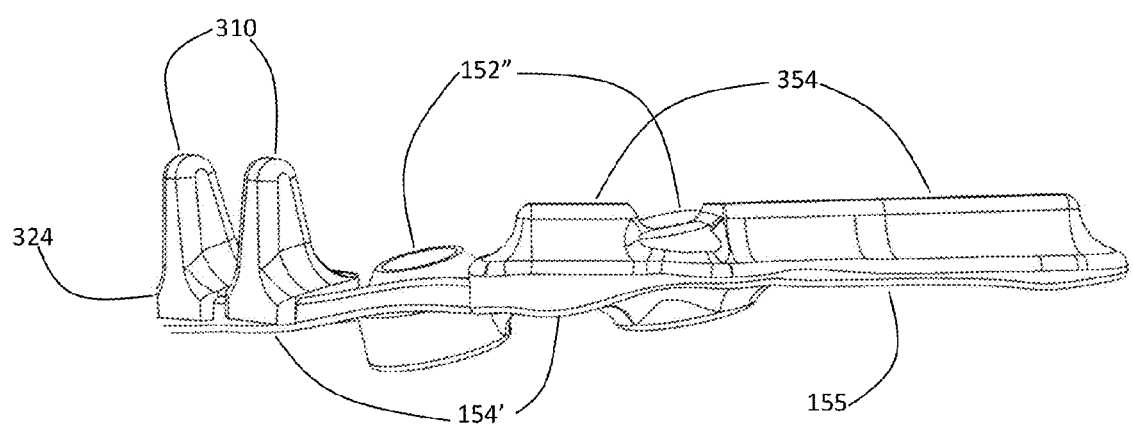
FIG. 22 is a side view of the framework model with a PTF bridging structure.
Figure 23A:
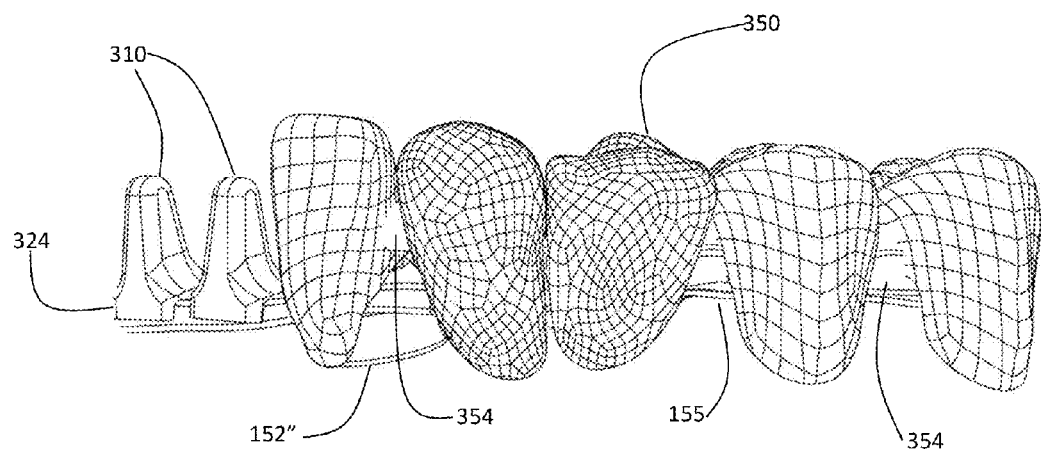
FIG. 23A is a side view of the framework model with the associated bridge model appropriately aligned together.
Figure 23B:
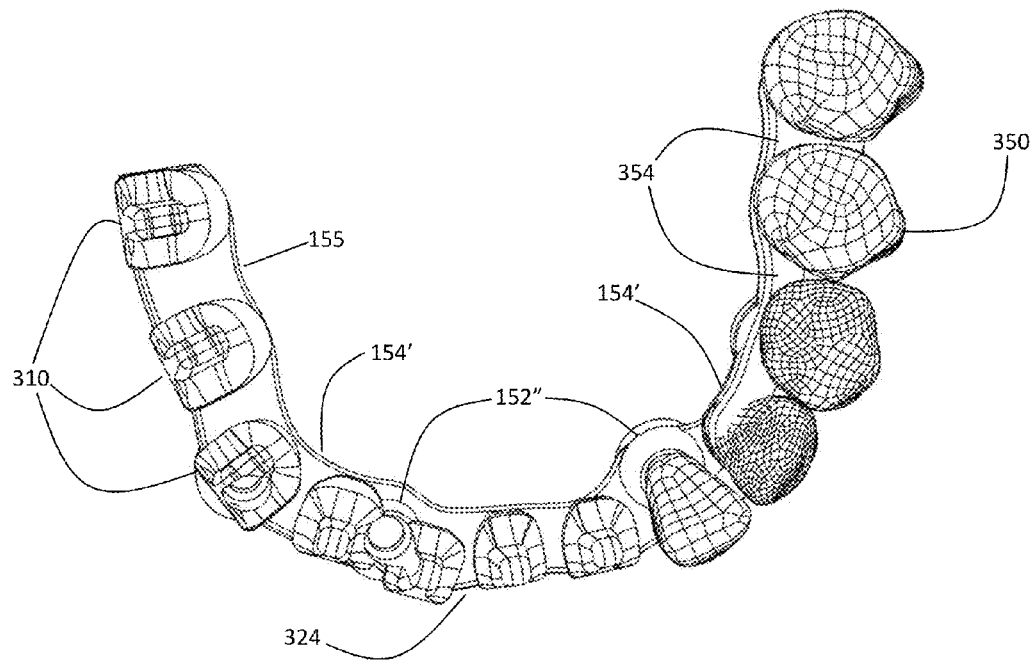
FIG. 23B is a top view of the framework model with the associated bridge model appropriately aligned together.

The operator may also determine it be best for the PTF's 310 be linked to one another in creating a larger support post geometry to support the overlying bridge. In the same manner that the bridging structures 154' are extended between the PTF's 310 and digitally parameterized fittings 152", a PTF bridging structure can be incorporated into the design either automatically by computer 186 or manually by the operator. This PTF bridging structure can consist of a standardized profile (e.g., a cylinder, circle, ellipse, square, polygon or other geometric shape) or the Operator can custom design an appropriate structure based upon the patients clinical conditions. The PTF bridging structure can have a constant cross-section or allow for portions of the PTF bridging structure to taper in from the buccal/lingual aspects to provide additional anti-rotation features when the overlying crowns or bridges are positioned on them appropriately. FIG. 22 shows a portion of framework model 324 with a PTF Bridging Structure 354 that has been created to support bridge 350. The PTF bridging structure extends across digitally parameterized fitting 152" in order to provide the necessary support for bridge 350. Due to the position of digitally parameterized fittings 152" and the resulting screw access holes, the standard PTF's were reduced drastically requiring for the creation of bridge 350 and the PTF bridging structure 354. FIG. 23 A-B show framework model 324 with bridge 350 properly positioned to one another.

It is also at this time that the Operator can choose to combine portions or the majority of the diagnostic wax-up surface model 322 to the crowns and/or bridge, to ensure the gingiva contours are included in the design. This process may be advantageous where there is limited vertical space associated with the patient. In having the gingiva contours incorporated into the design, the operator can ensure the gingiva will have substantial strength characteristics as it is joined and fabricated from the same material as the crown or bridge. In the case of a full Zirconia restoration, the technician can apply coloring through stains and dyes in order to create the aesthetics for both the gingiva and crown portions. In addition to combining portions of the diagnostic wax up to the crowns in creating the gingival structures, the operator can choose to design custom gingiva features onto the crown utilizing the tools in the design software. This process would allow the operator to modify the contours to best meet the clinical demands of the case or to provide the best foundation for the finishing processes to be performed after the crown/bridge with gingiva has been fabricated. One example would be in the creation of gingival contours that would be ideal for porcelain stacking. Rather than having the exact contours of the diagnostic wax-up surface model 322, the preferred geometry may be the creation of a small shelf with the buccal aspect of the gingiva contour reduced slightly to accommodate the added thickness of the porcelain. The Operator could determine the appropriate dimension for the necessary porcelain, for example 1-2 mm, and create the appropriate trim or Boolean subtraction to reduce the gingiva contour from the diagnostic wax-up surface model 322 or custom design the appropriate gingiva construct manually using the CAD tools provided in the software.

In STEP 234, tool paths are generated for the surface model of the framework 324, crown models 312 and/or bridges 350. Since the orientation and position of the framework and crowns has been determined along with the orientation and position of the DPF's 152" and margins 162 (where the crowns mate to the framework), both the framework and crowns can be manufactured simultaneously in the chosen material (titanium, cobalt chrome, zirconia, wax, plastic, composites, acrylic, lithium disilicate, plastic, PMMA, resin ceramic (Lava-Ultimate, Vita-Enamic) etc. . . . ) and through the preferred manufacturing process (milling, laser sintering, 3D printing, EDM, etc. . . . ).

Once the framework and crowns have been manufactured, they are delivered to the dentist and/or technician for the creation of the gingiva contours. The gingiva contours can be created by applying acrylic, composites, porcelain, or any other preferable dental material to the framework. If the gingiva contours were included in the design of the crowns, the technician will perform the necessary processing (i.e. staining, coloring, stacking porcelain, adding acrylic or composite . . . ) to complete the gingiva aesthetics.

The above disclosed invented process utilizes a traditional diagnostic wax-up 130, which provided the position of denture teeth 132 and ultimately PTF's 310 and crown models 312. In the first alternate embodiment of the process outlined in application Ser. No. 14/272,566, the use of a virtual set up is used in place of the diagnostic wax-up 130. There are currently multiple dental systems and software (such as 3Shape, Dental Wings, Avadent and Procera) which have the ability to lay in CAD models of denture teeth or stock teeth relative to scans of a stone cast and an opposing dentition. For this first alternate process, the stone cast and opposing cast would be scanned separately and then scanned in their proper orientation relative to one another. Utilizing the scan capturing the orientation of the stone cast and opposing cast, the scan data of the stone cast and opposing cast will be properly aligned to one another. Once properly aligned, the Operator will position the CAD models of the denture teeth or stock teeth relative to the occlusion of the opposing cast. Once the position of the CAD models of the denture teeth or stock teeth have been finalized, this information can be used in aligning the crown and PTF assemblies 316 and begin designing the crowns and framework. In addition to utilizing the CAD models of the denture teeth or stock teeth, the operator can immediately begin utilizing the library of crown and PTF assemblies 316 and align the assemblies relative to the opposing cast for the proper orientation. This process may be advantageous over the previous described process as it alleviates the dentist and/or technician from having to create the diagnostic wax up. Also if the crown models are truly parametric, the operator can modify the design of the occlusal contours and buccal contours of the desired crown to meet any unique design requirements for the dentist.

In the second alternate process outlined in application Ser. No. 14/272,566, the scanning process for capturing the implant and abutment positions is altered by the use of an intra-oral scanner that would directly capture the implant and/or abutment locations in the patient's mouth along with the gingiva contours. The intra-oral scanner can also capture the contours of a diagnostic wax up that has been placed in the patient's mouth or the position and orientation of the opposing arch during the scanning process. From this digital data, the dentist or technician can identify the appropriate location of the crown/PTF assemblies 316 and digitally parameterized fittings 152". This process would alleviate the dentist or technician from being required to create an impression or stone cast.

In a third alternate process outlined in application Ser. No. 14/272,566, the dentist or technician can utilize a CT scan or series of CT scans for the basis of determining the appropriate position of the crown/PTF assemblies 316 and the digitally parameterized fittings 152". The dentist or technician can use the CT scan data for determining or planning the position of the implant locations and ultimately the position of the digitally parameterized fittings 152". The use of a radiographic stent demonstrating the ideal tooth position for the restoration can also be included in this process and provide the dentist and technician with an ability to align the crown/PTF assemblies 316 relative to the contours of the radiographic stent or relative to the position of the opposing arch. The dentist or technician could also utilize a CT scan of the patient's previous existing dentition, which could be aligned utilizing anatomical markers, in order to determine the ideal position of the crown/PTF assemblies 316.

These alternate embodiments only demonstrate some of the potential options in combining different digital data acquisition protocols into the invented process. As can be appreciated, these are only a handful of potential embodiments of the invented process, but should provide insight as to the adaptation of future technologies.

The above descriptions, alternate embodiments and processes described and outlined in application Ser. No. 14/272, 566 can be appreciated for its ability in providing an improved functional and aesthetic restoration for cases with large vertical dimensions. For patients exhibiting a much smaller vertical dimension (less than 10 mm), the functional or aesthetic characteristics of the resulting restoration may not be ideal. We have already discussed the issues surrounding traditional hybrid designed prosthesis utilizing denture teeth and processed acrylic in reduced vertical dimensions where acrylic breakage is a common problem. For Individual crown type restorations, the issue of reduced vertical dimensions provides a unique challenge where the designer does not have the appropriate space for the fabrication of the individual support post or PTF's and providing crowns with an appropriate wall thickness to prevent breakage. An additional concern in reducing the wall thickness of the crowns is the potential show through of the underlying support post, which may affect the shade of the prosthesis. The proposed invention is to provide an improved prosthesis and process over any of the previously described in dealing with reduced vertical dimensions.

Figure 12B:
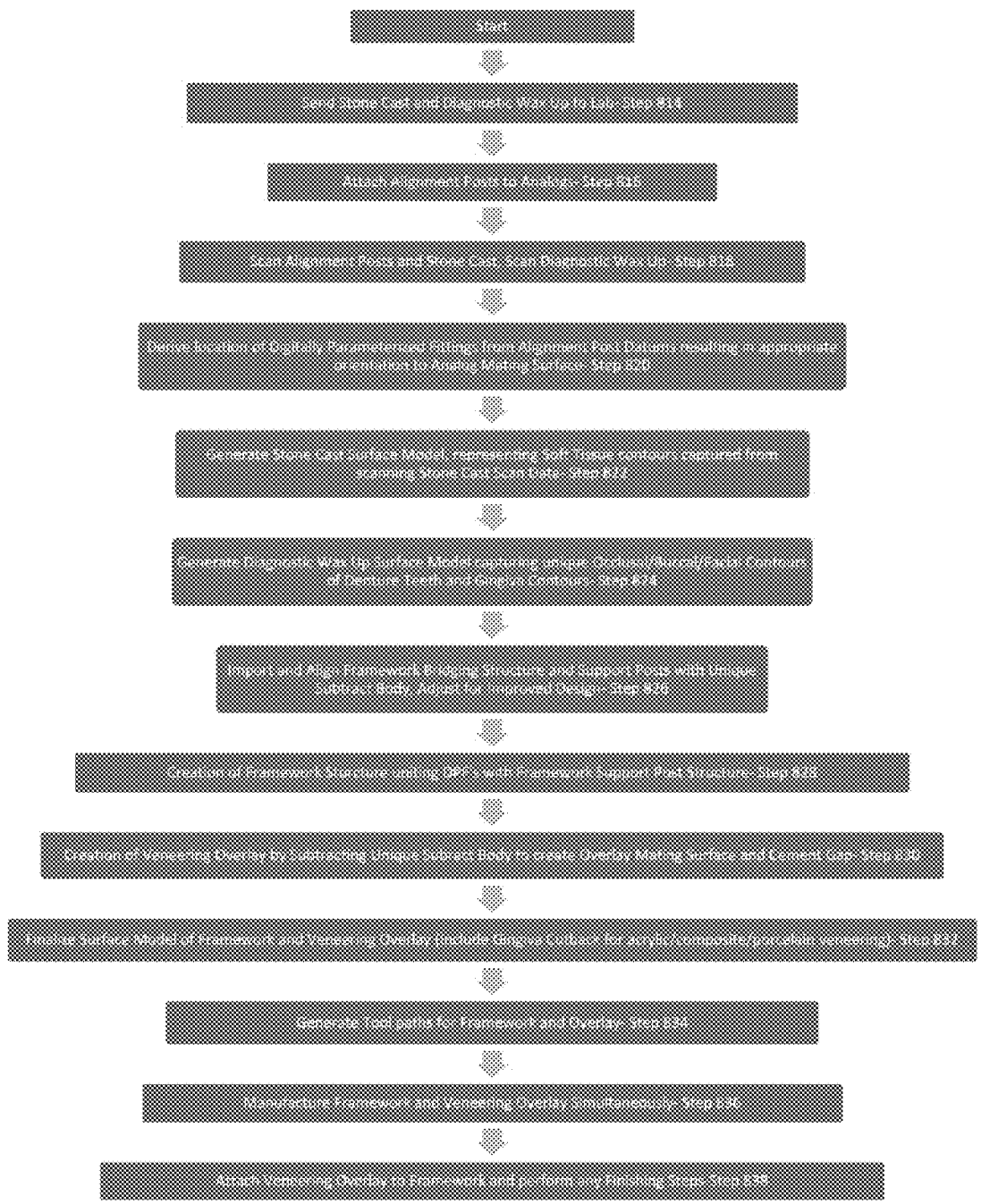
FIG. 12B is a flow chart demonstrating the steps for the new invented process and invention.

The preferred embodiment of the invention consists of a framework fabricated form a dental material (titanium, cobalt chrome, semi-precious metals, precious metals, zirconia, lithium disilicate, ceramic, PMMA, composite, plastic, acrylic, wax, etc. . . . ) that supports a veneering overlay consisting of a second dental material (titanium, cobalt chrome, semi-precious metals, precious metals, zirconia, lithium disilicate, ceramic, PMMA, composite, plastic, acrylic, wax, etc. . . . ). FIG. 12B outlines the steps for designing and fabricating the preferred embodiment of the invention. Similar to the process outlined in application Ser. No. 14/272,566, alignment posts 156 are attached to the analogs 124 of stone cast 125 and scanned where computer 186 determines the location and orientation of the alignment posts and sequentially selects and aligns digital parameterized fitting 152" based upon datums derived from the alignment posts 156. Diagnostic wax-up 130 is also scanned either properly positioned on stone cast 125 or separately and then aligned to stone cast 125 utilizing the surface contour of the diagnostic wax-up 130 that abut the stone cast as they are a mirror image of surface contours of the stone cast 125. When the diagnostic wax-up is scanned it is critical to capture the contours of the denture teeth and gingiva as these contours will be replicated in the veneering overlay. Surface models of the stone cast (320) and diagnostic wax-up (322) are generated on the basis of the scan data. These surface models are constructed in such a way as to allow for Boolean Unite, Subtract, and Trim Operations to be performed utilizing these models or other CAD bodies. The above listed processes are outlined in Steps 814-824 of FIG. 12B.

Figure 24A:
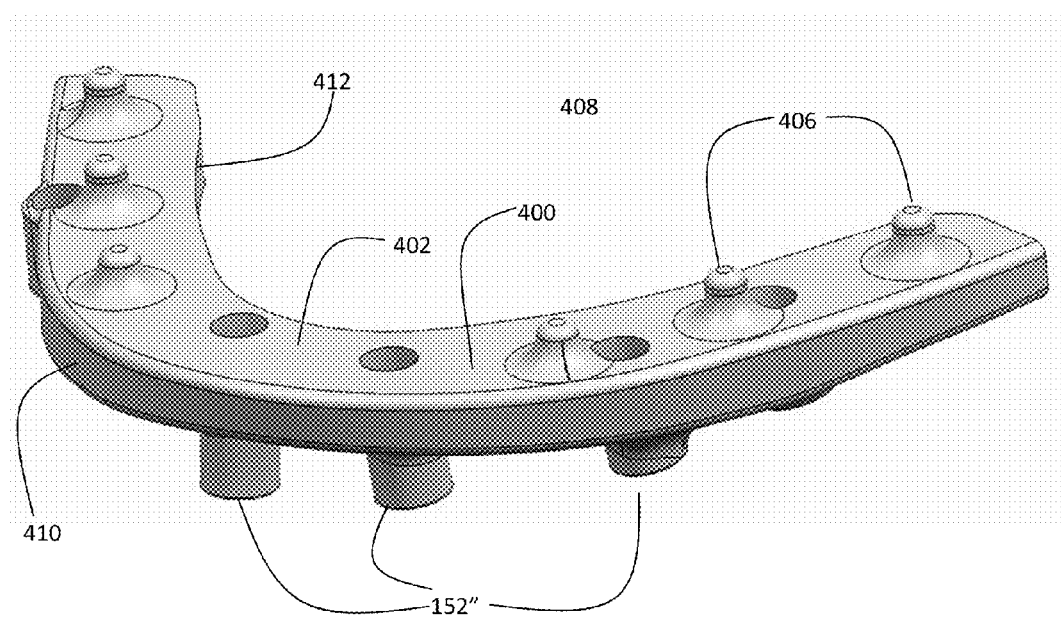
FIG. 24A is a perspective view of the framework designed to support the veneering overlay.
Figure 24B:
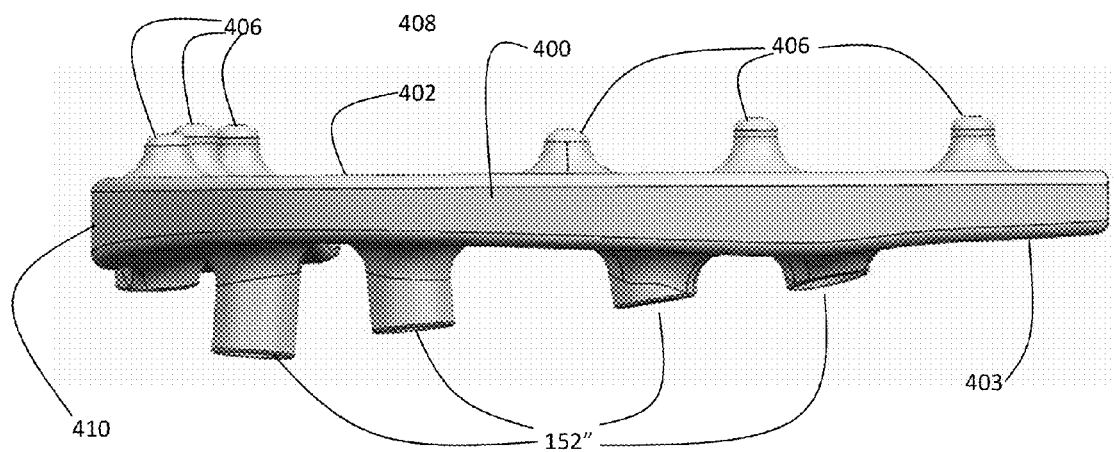
FIG. 24B is a side view of the framework designed to support the veneering overlay.

Once all of the scan data, surface models (320 and 322) and digital parameterized fittings 152" have been aligned properly to one another, computer 186 imports and appropriately aligns framework bridging structure 400 relative to the digital parameterized fittings 152", stone cast surface model 320 and diagnostic wax-up surface model 322 as noted in STEP 826. This step can also be performed manually by the operator. The framework bridging structure 400 consists of a predefined cross-section and possesses parametric attributes allowing for portion of the framework bridging structure to be adaptable to the unique contours of the diagnostic wax-up and stone cast surface models. In the preferred embodiment the framework bridging structure consists of a rectangular cross-section and can vary in height and length depending upon the contours of the surface models 320 and 322. In some areas the bar may be taller than others due to the changes in the patient's soft tissue that are captured in the stone cast surface model 320. In other areas the bar may be wider than others due to the varying contours of the diagnostic wax-up surface model 322. Frequently the width of the diagnostic wax-up 130 is greater in the posterior regions, where the molar teeth reside in comparison to the anterior where you will find the incisors. Ideally the top surface of the framework will remain on a single plane, but this top surface can be offset in certain areas due to fluctuations of the vertical dimension in the patient's mouth. This top surface 402 will support and engage the resulting veneering overlay 404. The position and angulation of this top surface 402 can be adjusted automatically by computer 186 or by the operator to meet either the clinical demands for the dentist and technician or for ease in manufacturing. The position of this top surface 402 can be positioned substantially into the area where the denture teeth reside in the diagnostic wax-up 130. This design feature is possible as the veneering overlay 404 will be fabricated from a single monolithic piece. The buccal wall 410 of framework bridging structure 400 will be positioned ideally 1-4 mm from the buccal aspect of the diagnostic wax-up surface model 322. This required clearance allows for an appropriate amount of material to prevent any potential show through of the framework through the veneering overlay 404. The operator or computer will also adjust the bottom surface 403 of the bridging structure to have the appropriate clearance or contact with the gingiva contours as captured in the stone cast surface model 320. The stone cast surface model 320 can also be used as a Boolean CAD Tool to contour the bottom of the bar to match gingiva contours in the patient's mouth by means of a Boolean Subtract operation. In the preferred embodiment of the invention, the buccal wall 410 is typically flat and held at a 90 degree angle relative to the top surface 402. This design aspect provides an ease in milling and fabrication. Obviously this wall angle could be adjusted to meet the technical demands of the dentist or technician or due to a limitation associated with the case. In the preferred embodiment, the lingual wall 412 of the framework bridging structure 400 will be adjusted to terminate at the lingual boundary of the diagnostic wax-up surface model 322 and can be flush with this boundary. The lingual wall 412 can be flat similar to the buccal wall 410 or even rounded if preferred by the dentist and/or technician. However using Boolean Unite, Subtract, and Trim Operations in the CAD software the lingual wall 412 can be shaped to exactly replicate the boundary of the diagnostic wax-up surface model 322 and follow the exact lingual contours as created in diagnostic wax-up 130 by the dentist. FIGS. 24A and 24B depict an embodiment of the framework 408. As demonstrated by these figures, digital parameterized fittings 152" has been united through a Boolean Unite Operation to framework bridging structure 400, as noted in Step 828. In this embodiment, the digital parameterized fittings 152" are substantially within the body of the framework bridging structure 400. In some embodiments these digital parameterized fittings 152" may extend through or slightly out of the framework bridging structure 400.

As part of the framework bridging structure, one or more support posts 406 can be positioned on top surface 402. Support posts 406 provide macro retention and resistance against lateral forces between the framework bridging structure 400 and the veneering overlay 404. The support posts 406 can be imported as part of framework bridging structure 400 or imported separately. The preferred design of the support posts 406 is a design consistent with a cylinder, which can be easily milled or fabricated by a known method (laser sintering, wire EDM, etc. . . . ), but can consist of any number of different cross-sections as desired by the operator, e.g., a cylinder, circle, ellipse, square, polygon or other geometric shape. In addition to the support posts, the design can consist of slots or recesses on the buccal wall 410 or lingual wall 412. The combination of framework bridging structure 400, digital parameterized fittings 152" and the associative retention features (support posts 406 or other retention features) creates the complete embodiment of the dental implant framework 408.

As the framework bridging structure 400 is being designed, the veneering overlay 404 is being designed simultaneously. The veneering overlay 404 is created directly from diagnostic surface model 322, by the use of a Boolean subtract operation and a unique subtract body related to the framework bridging structure 400. As discussed in application Ser. No. 14/272,566 where the crowns, margins, and cement gaps are updated by the repositioning of the PTF or support post, the unique mating surface of the veneering overlay 404 is updated/refined by a unique subtract body that is dependent upon the design features of framework bridging structure 400 and digital parametrized fittings 152" (top surface 402, support posts 406, buccal wall 410, lingual wall 412, slots, recesses etc.). The subtract body creates the necessary overlay mating surface 402' and the appropriate clearance gaps 414 that provide the necessary space and clearance between buccal wall 410, parameterized fittings 152", and protrusions 406. Clearance around the buccal wall 410, parameterized fittings 152", and protrusions 406 allows for an intimate mating of the overlay mating surface 402' to the top surface 402 of the framework bridging structure 400. This design aspect allows for an appropriate transfer of occlusal forces from the veneering overlay 404 to the top surface 402 of framework bridging structure 400 and ultimately to the dental implants in the patient's mouth. This clearance gap 414 also provides a space where a bonding agent such as cement, acrylic, heat cured bonding agent, chemical bonding agent (epoxy) can be used to permanently retain the veneering overlay 404 to framework 408. The subtract body for veneering overlay 404 can also include bodies for the parameterized fittings 152" and screw access holes 418 to be subtracted from the veneering overlay 404. This design feature allows for the dentist to access the screws retaining the framework to the implants without having to remove the cemented veneering overlay 404. However at times the dentist may choose to bond the veneering overlay 404 in the patient's mouth either due to aesthetic demand or issue with a screw access hole coming through a buccal aspect of the prosthesis. The previous description describes a design where the veneering overlay 404 is retained to framework 408 by means of a bonding agent, which is the preferred method. Bonding agents, such as cement, allow for the restoration to work in the smallest restorative spaces possible and permanently fixates the veneering overlay to the framework, which allows for the most optimal performance of the restoration in the patient's mouth. It is obvious that other means of retention such as the use of screws, mechanical clamps, or memory alloy clamps (U.S. Pat. No. 8,678,822) could also be used in retaining the overlay to the framework if space allows, but these mechanical retention means can deteriorate over time and be costly in replacing. If a mechanical retention means is used, the dentist or technician would still want to apply a material (silicone) that would seal the clearance gap between the veneering overlay 404 and framework 408.

Figure 25A:
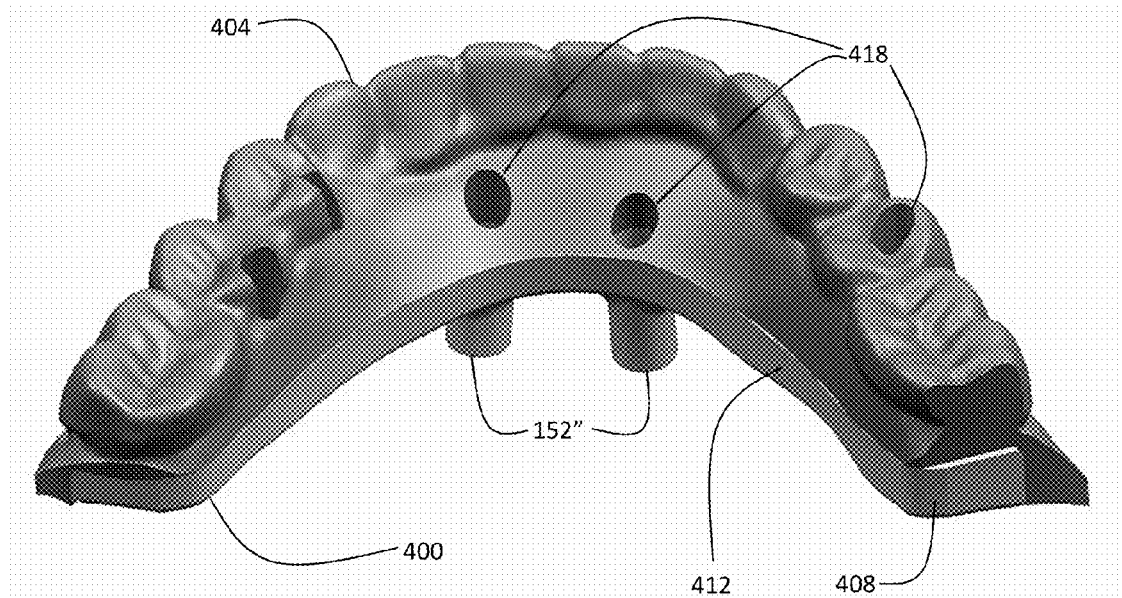
FIG. 25A is a back side view of the framework and the veneering overlay appropriately aligned and mating with one another.
Figure 25B:
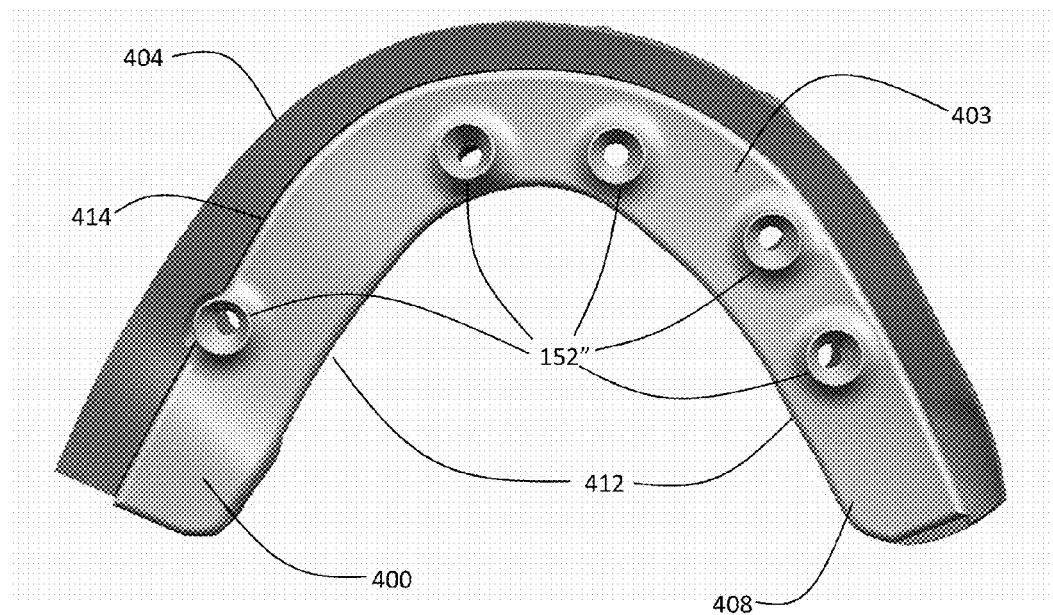
FIG. 25B is a bottom side view of the framework and the veneering overlay appropriately aligned and mating with one another.
Figure 25C:
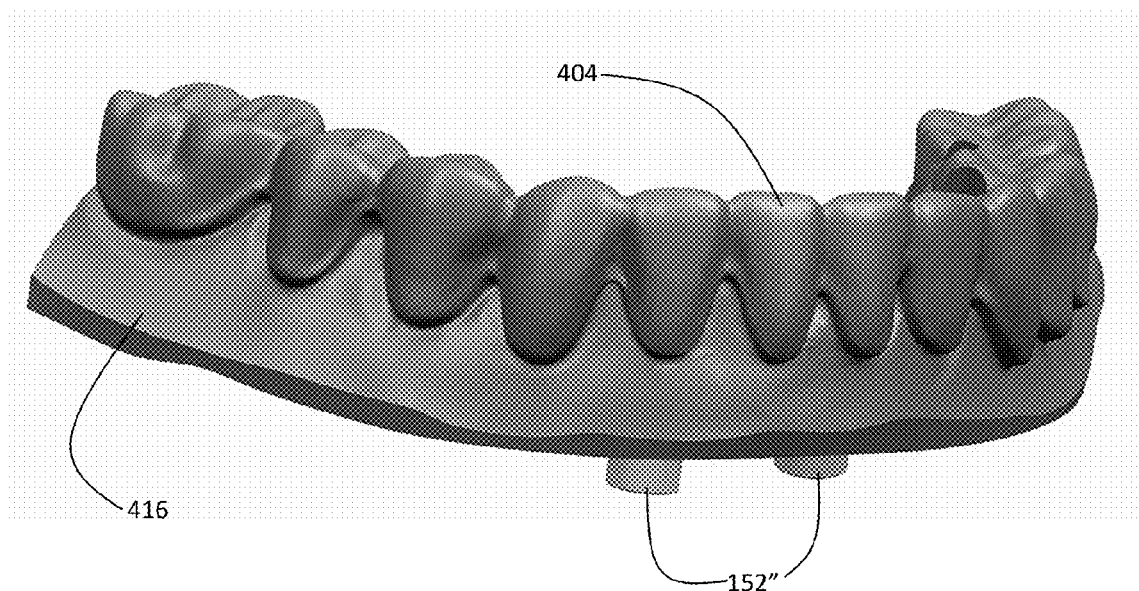
FIG. 25C is a perspective view of the framework and the veneering overlay appropriately aligned and mating with one another.
Figure 25D:
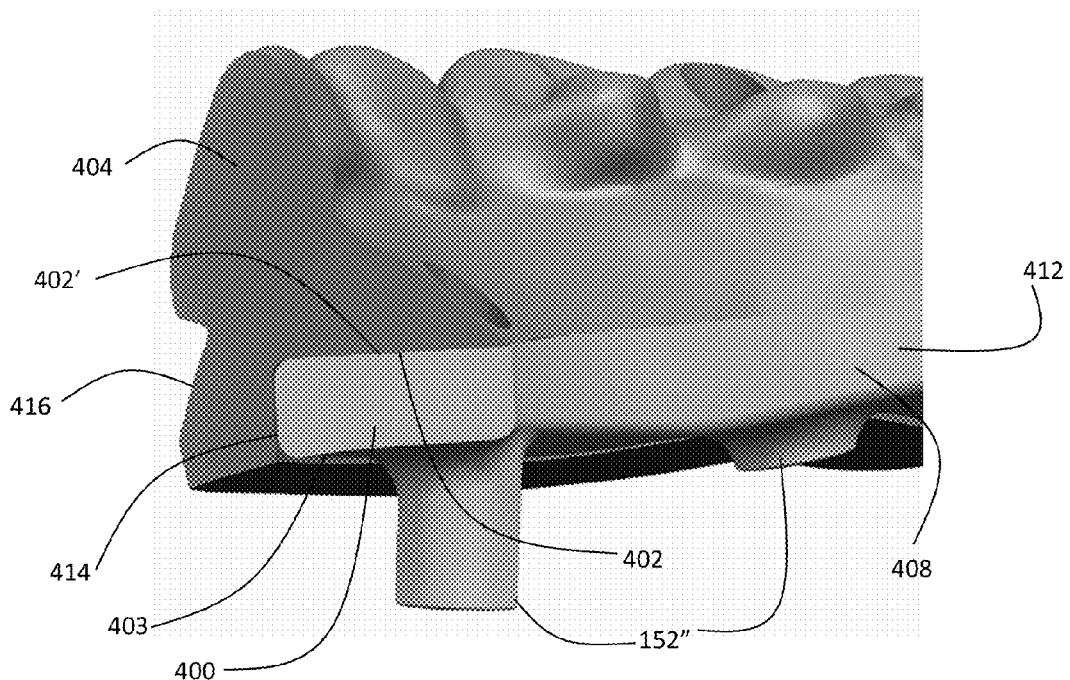
FIG. 25D is a cross-sectional view of the framework and the veneering overlay appropriately aligned and mating with one another.
Figure 25E:
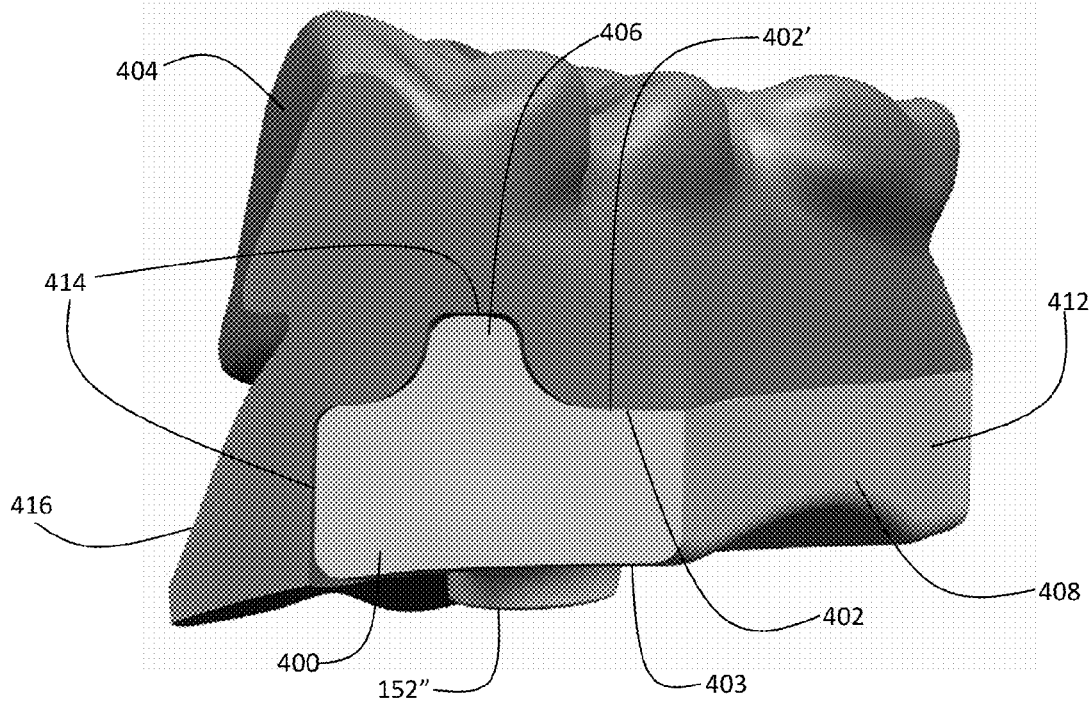
FIG. 25E is a second cross-sectional view of the framework and the veneering overlay appropriately aligned and mating with one another and demonstrating the cement gap pertaining to the protrusion on the top surface of the framework.

FIGS. 25A, B, C, D and E depict the preferred embodiment of the invention as described above and demonstrates the framework bridging structure 400, veneering overlay 404, the mating surface 402', top surface 402, support posts 406, buccal wall 410, lingual wall 412 and clearance gap 414. FIGS. 25D and E are cross-sectional views of the framework 408 and veneering overlay 404 and demonstrate the areas where clearance gap 414 are positioned relative to the two parts. In the preferred embodiment depict in these figures, the lingual wall of the framework is exposed. This feature is aimed in simplifying the operations associated with fabricating the framework and veneering overlay. The lingual wall 412 and the bottom surface 403 of the framework 408 may be polished and left exposed or the technician may choose to apply a dental material such as composite or acrylic to wrap and seal these surfaces. Some doctors prefer this type of design as it allows them to adjust or add to this surface as the patient's gingiva contours may change over time. This additional work can be done at the same time that any other required finishing steps are performed prior to delivering the restoration to the patient's mouth. The design of the veneering overlay 404 can also be altered by covering the lingual wall 412. The unique subtract body would need to be slightly altered to accommodate this design feature in creating the appropriate clearance between the lingual wall 412 and veneering overlay 404.

Figure 26A:
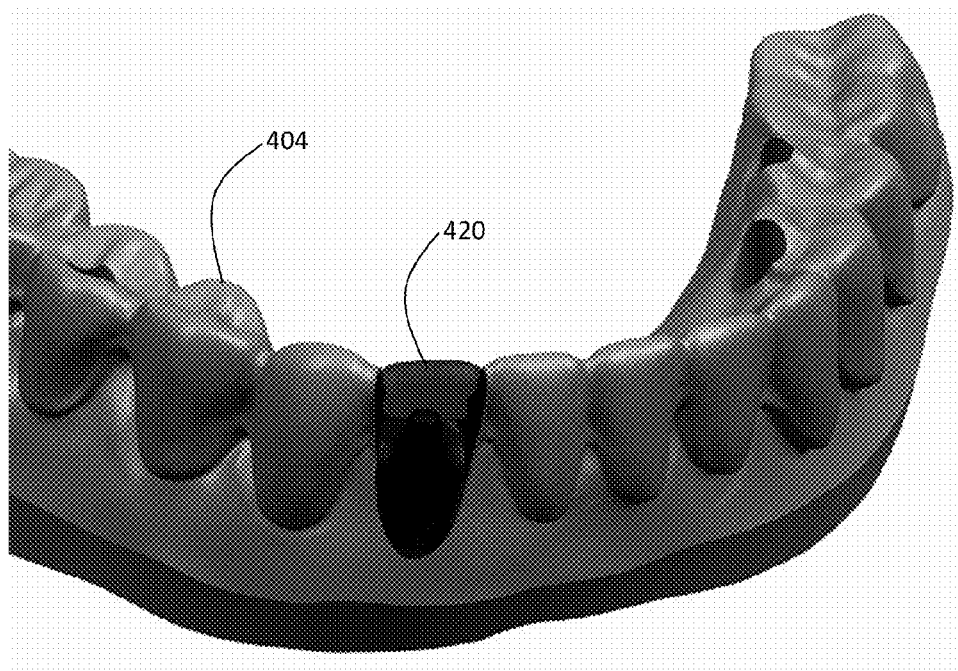
FIG. 26A is a perspective view of the framework, the veneering overlay, and crown appropriately aligned and mating with one another.
Figure 26B:
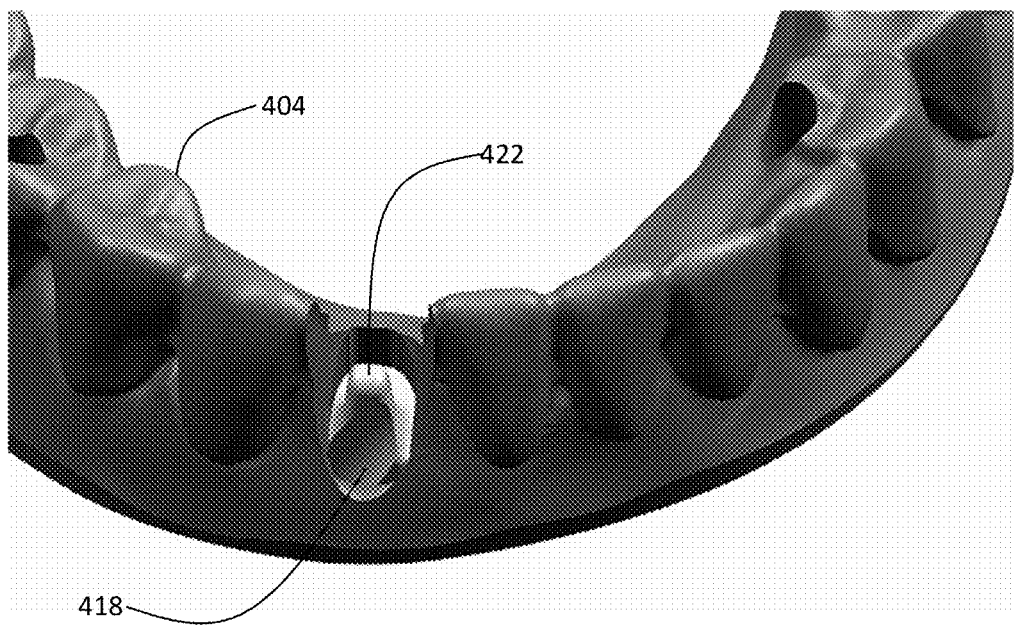
FIG. 26B is a perspective view of the framework and the veneering overlay appropriately aligned and mating with one another and with the PTF of the framework extending through the veneering overlay.
Figure 26C:
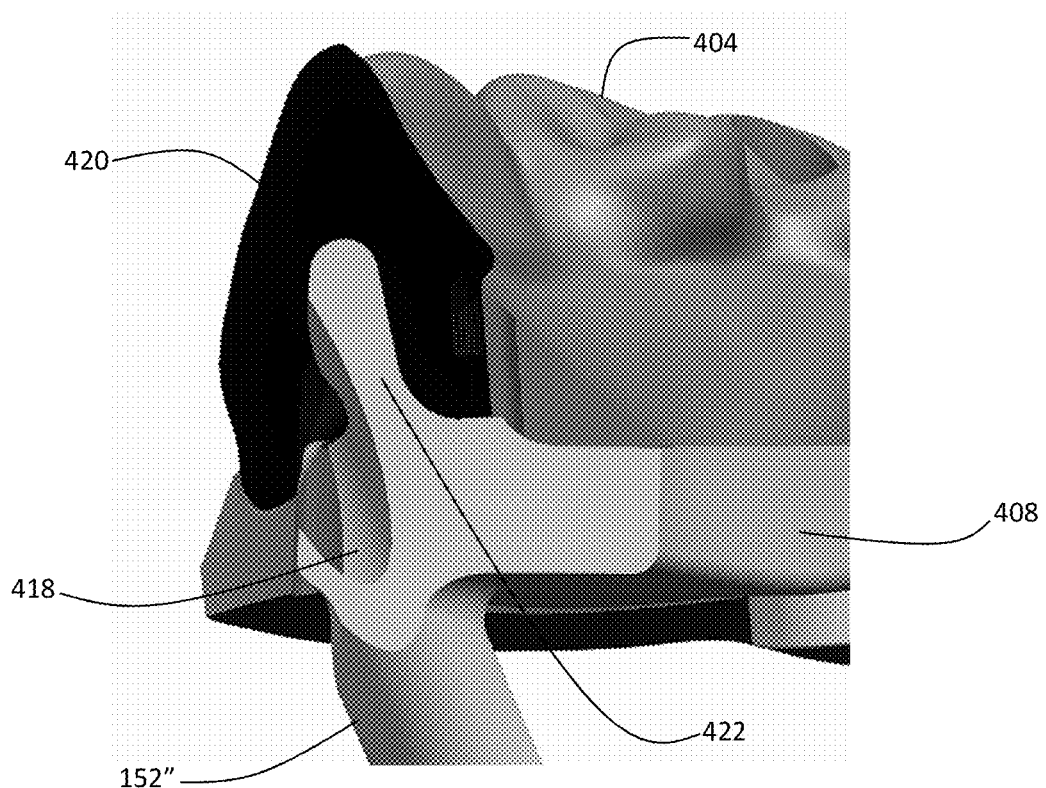
FIG. 26C is a cross-sectional view of the framework, the veneering overlay, and crown appropriately aligned and mating with one another, with the crown mating to the PTF associated with the framework.
Figure 26D:
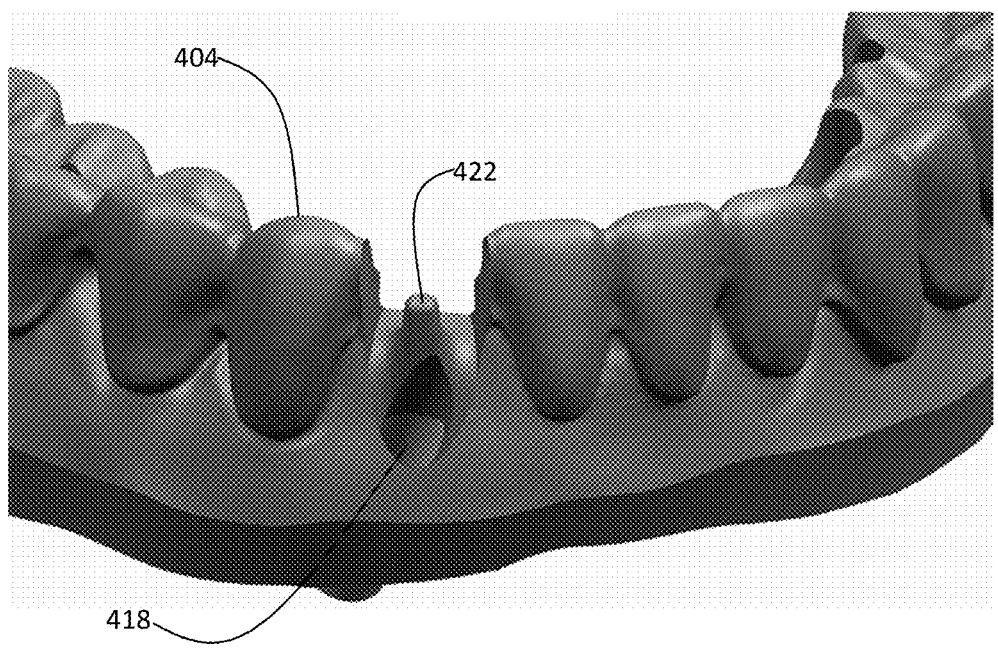
FIG. 26D is a perspective view of the framework and the veneering overlay appropriately aligned and mating with one another and with the PTF as part of the veneering overlay.
Figure 26E:
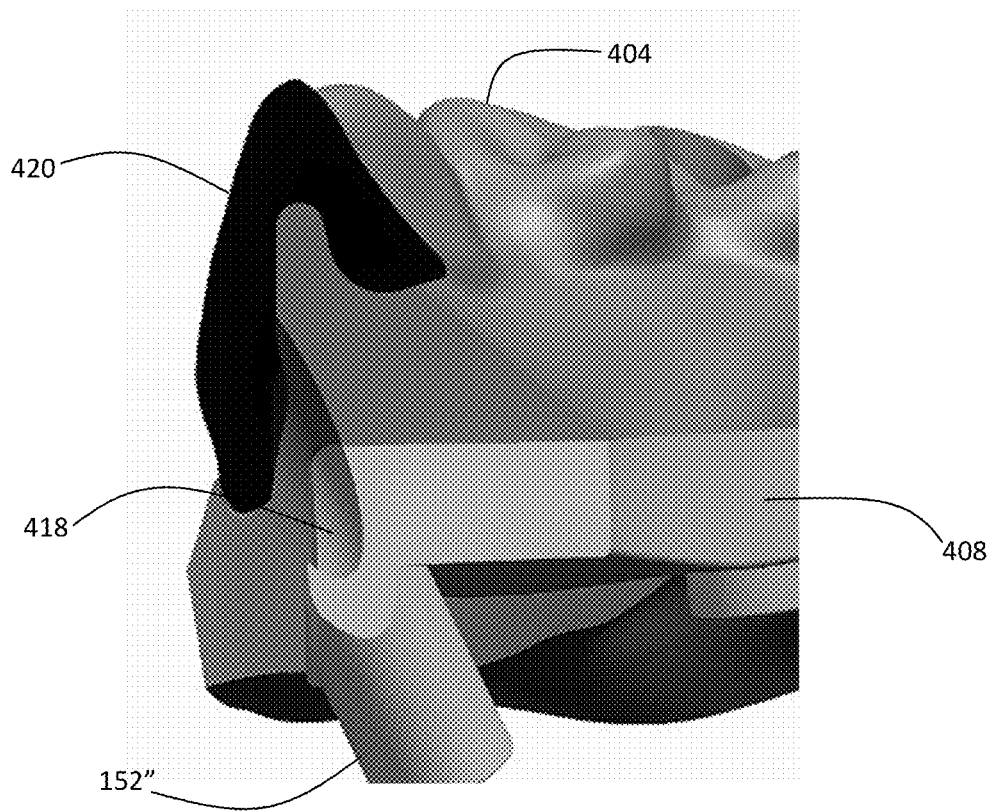
FIG. 26E is a cross-sectional view of the framework, the veneering overlay, and crown appropriately aligned and mating with one another, with the crown mating to the PTF associated with the veneering overlay.

In addition to cementing the veneering overlay 404 in the patient's mouth to avoid the poor aesthetics, a "prep tooth form" or "PTF" can be designed into the framework bridging structure or into the veneering overlay to support a single crown, veneer or bridge to cover the screw access hole. FIGS. 26A, B, and C depict a crown 420 being placed onto a PTF 422 that is part of the framework bridge structure 400. In FIGS. 26D and E demonstrates a crown being supported by a PTF 422 that is part of the veneering overlay 404. One benefit in designing PTF 422 as part of veneering overlay 404 is crown 420 and veneering overlay 404 can be fabricated from similar materials, such as Zirconia and allow for an improved shade match. In a similar fashion as discussed in patent application Ser. No. 14/272,566, the crown/PTF Assembly can be aligned relative to the contours of the diagnostic wax-up surface model 322. Once properly positioned, the PTF 422 and spacing/cement gap for the crown, veneer, or bridge in the veneering overlay 404 can be created by using Boolean Unite, Subtract, and Trim Operations in the CAD software. This process does not have to be limited to just areas where there is an issue with the screw access hole. This operation or design can be conducted throughout the entire prosthesis and allow for the utilization of different dental materials on the basis of the patient's clinical demands or doctor's preferences.

As previously mentioned, the veneering overlay 404 is created from the diagnostic wax up surface model 322 which captured all of the surface characteristics of the teeth and gingiva contours of diagnostic wax up 130. These contours can be left intact and the operator or technician can use a series of stains to color these contours to the appropriate shade per the material that the veneering overlay is fabricated from. However the veneering overlay 404 can be further refined to allow for additional laboratory processing such as the application of porcelain, composite, acrylics, or other dental materials to aid in the aesthetics of the final prosthesis. Additional Boolean or offset operations can be performed to the surface contours of the teeth or gingiva in the veneering overlay 404 to create a cutback 416 allowing for the appropriate support structure and space for these materials to be applied post fabrication. This process allows the laboratory technician to have a higher level of control on the look, shade and aesthetics of the final prosthesis. This process can also be performed on the tooth aspect of the overlay, again allowing for the technician to apply porcelains, composites, acrylics, or other dental materials to aid or improve the aesthetics of the final prosthesis. FIGS. 25A-E and 26A-E demonstrate a cutback for the gingiva only. It is obvious to one trained in the art, that a similar cutback could be performed to the tooth portions of the veneering overlay 404.

Once the surface models for both the Framework 408 and veneering overlay 404 have been finalized as noted in Step 832 the appropriate tool paths can be generated (Step 834) for the simultaneous manufacturing (Step 836) of both items. For fabrication purposes, one can choose from a number of different methodologies such as but not limited to milling, laser sintering, 3D printing, ceramic pressing, EDM, etc. . . . . The framework and veneering overlay can also be manufactured from a number of materials such as but not limited to titanium, cobalt chrome, semi-precious metals, precious metals, zirconia, wax, plastic, composites, acrylic, PMMA, resin ceramic (Lava-Ultimate, Vita-Enamic) etc. . . . . Once the framework 408 and veneering overlay 404 have been manufactured, the operator can perform any of the necessary finishing activities and attach the veneering overlay to the framework by means of a bonding agent or other means of retention.

In addition, the veneering overlay 404 may be manufactured directly to framework 408. In one example the Veneering Overlay can be printed directly onto the framework in the appropriately selected materials. A second example would be first milling the Veneering overlay in a wax material and then through the use of a lost wax technique, the veneering overlay portion can be cast directly to the framework. Obviously these process would involve additional work to refine the aesthetics before delivering to the patient's mouth.

In the first alternate embodiment of the invented process, the use of a virtual set up in place of the diagnostic wax-up 130. There are currently multiple dental systems and software (such as 3Shape, Dental Wings, Avadent, Ivoclar and Procera) which have the ability to lay in CAD models of denture teeth or stock teeth relative to scans of a stone cast and an opposing dentition. For this first alternate process, the stone cast and opposing cast would be scanned separately and then scanned in their proper orientation relative to one another. Utilizing the scan capturing the orientation of the stone cast and opposing cast, the scan data of the stone cast and opposing cast will be properly aligned to one another. Once properly aligned, the Operator will position the CAD models of the denture teeth or stock teeth relative to the occlusion of the opposing cast or anatomical markers found on the casts. The operator can also adjust the occlusion by tools provided in the software. Once these CAD models have been properly positioned, the gingiva contours of the prosthesis can be constructed. This resulting model can be used in the same fashion as the diagnostic wax-up surface model 322 in the above described process and provide the tooth and gingiva contours for the veneering overlay 404. The software programs also have tools that would allow for the appropriate design or construction of a gingiva or tooth cutback design allowing for the application of acrylic, composites, porcelain or other dental material to improve the aesthetics of the case.

In the second alternate process, the scanning process for capturing the implant and abutment positions is altered by the use of an intra-oral scanner that would directly capture the implant and/or abutment locations in the patient's mouth along with the gingiva contours. The intra-oral scanner can also capture the contours of a diagnostic wax up that has been placed in the patient's mouth or the position and orientation of the opposing arch during the scanning process. From this digital data, the dentist or technician can identify the appropriate location of the digitally parameterized fittings 152" and generate the stone cast surface model 320 and the diagnostic wax-up surface model 322. This process would alleviate the dentist or technician from being required to create an impression or stone cast.

In a third alternate process, the dentist or technician can utilize a CT scan or series of CT scans for the basis of determining the appropriate position of the digitally parameterized fittings 152". The dentist or technician can use the CT scan data for determining or planning the position of the implant locations and ultimately the position of the digitally parameterized fittings 152". The use of a radiographic stent demonstrating the ideal tooth position for the restoration can also be included in this process and provide the dentist and technician with an ability to create the diagnostic wax-up surface model 322 relative to the contours of the radiographic stent or create a virtual set up relative to the position of the opposing arch. The dentist or technician could also utilize a CT scan of the patient's previous existing dentition, which could be aligned utilizing anatomical markers, in order to create the diagnostic wax-up surface model 322.

These alternate embodiments only demonstrate some of the potential options in combining different digital data acquisition protocols into the invented process. As can be appreciated, these are only a handful of potential embodiments of the invented process, but should provide insight as to the adaptation of future technologies.

What is claimed:

1. A dental prosthesis for restoring the appearance and function of a patient's missing teeth comprising a veneering overlay, a dental implant framework and a series of implants and abutments adapted to be placed within a patient's mouth, wherein the dental implant framework is intended to mate to the series of implants and abutments where the design of the veneering overlay and dental implant framework are based upon digital data obtained from the patient:
   the dental implant framework further comprising a plurality of fittings to mate with the corresponding implants and abutments in the patient's mouth;
   the dental implant framework further comprising a plurality of support posts to provide macro retention and resistance to lateral forces that are applied to the top surface of the dental implant framework;
   the dental implant framework further comprising a plurality of bridging structures to attach the support posts and fittings to one another;
   the veneering overlay further comprising a plurality of tooth contours and gingiva contours;
   the design of the veneering overlay and dental implant framework being determined from the digital data defining the appropriate tooth contours, gingiva contours and implant and abutment locations for the dental prosthesis;
   the veneering overlay further comprises a veneering overlay mating surface and a dental implant framework structure, wherein the dental implant framework structure comprises a dental implant framework mating surface and the veneering overlay mating surface and the dental implant framework mating surface further create a predefined mating surface and a clearance gap to allow for an appropriate mating of the veneering overlay to the dental implant framework;
   the veneering overlay mating surface is created on the basis of a unique subtract body that is dependent upon design features of the dental implant framework mating surface;
   the plurality of tooth contours and gingiva contours of the veneering overlay being derived from the digital data from the patient;
   the veneering overlay and dental implant framework being permanently fixated to one another.

2. The dental prosthesis of claim 1, where the veneering overlay is intended to intimately mate to the top surface of the dental implant framework.

3. The dental prosthesis of claim 2, wherein the position of the support posts is based upon the digital data of the tooth and gingiva contours.

4. The dental prosthesis of claim 2, wherein the veneering overlay and dental implant framework are fully parametric and easily edited during a design phase.

5. The dental prosthesis of claim 4, wherein the veneering overlay and dental implant framework features are dependent upon one another, wherein the dependency allows for changes in orientation, dimensions or features in either the veneering overlay or dental implant framework, and wherein the changes result in modifications in either the veneering overlay or dental implant framework, whichever was not changed.

6. The dental prosthesis of claim 1, wherein the digital data defining the appropriate tooth and gingiva contours are derived from one of the following; scanning a diagnostic wax up or denture tooth set up; CAD models in a virtual set up; an intraoral scan of a diagnostic wax up or denture tooth set up taken in the patient's mouth; a CT scan or series of CT scans of the patient's mouth; a CT scan or series of CT scans with the use of a radiographic stent in the patient's mouth.

7. The dental prosthesis of claim 2, wherein the veneering overlay includes gingiva contours as designed by an operator.

8. The dental prosthesis of claim 2, wherein the veneering overlay includes a cutback allowing for a technician to create the tooth or gingiva contours of the final prosthesis.

9. The dental prosthesis of claim 2, wherein the veneering overlay and dental implant framework are permanently fixated to one another by a bonding agent or a mechanical retention mechanism.

10. The dental prosthesis of claim 1, where the veneering overlay and dental implant framework can be manufactured simultaneously.

11. The dental prosthesis of claim 10, wherein the veneering overlay is fabricated out of one of the following; a metallic material; a ceramic material; an acrylic material; a biocompatible material.

12. The dental prosthesis of claim 10, wherein the dental implant framework is fabricated out of one of the following; titanium or other metallic materials; zirconia or other ceramic materials; acrylic or other composite materials; a biocompatible material.

13. The dental prosthesis of claim 2, wherein the veneering overlay includes the gingiva contours captured in the digital data defining the appropriate tooth and gingiva contours for the final dental prosthesis.

14. The dental prosthesis of claim 1, wherein the digital data for locations of the implants and abutments have been derived from one of the following; scanning the analogs in the stone cast of the patient; an intraoral scan of the implants and abutments in the patient's mouth; digital surgical planning of the proposed implant positions on the basis of a CT scan or series of CT scans; a CT scan or series of CT scans.

15. A dental implant framework intended to mate with a veneering overlay and a plurality of implants and abutments comprising:
a plurality of fittings to mate with and correspond with plurality of implants and abutments in the patient's mouth;
a plurality of support posts to provide macro retention and resistance to lateral forces applied to the top surface of the dental implant framework;
a plurality of bridging structures attaching the plurality of support posts and the plurality of fittings to one another;
wherein the design of the dental implant framework is determined from digital data obtained from the patient defining the appropriate tooth contours, gingiva contours and plurality of implant and abutment locations for a dental prosthesis;
wherein the combination of the plurality of bridging structure, plurality of support posts, and plurality of fittings providing the complete embodiment of the dental implant framework;
wherein the dental implant framework structure includes a predefined mating surface and clearance gap to allow for an appropriate mating of a veneering overlay to the framework;
where the mating surface of the veneering overlay is created on the basis of a unique subtract body that is dependent upon design features of the designed framework;
where the dental implant framework is constructed from available dental material; and
where the veneering overlay and dental implant framework are permanently fixated to one another.

16. The dental implant framework of claim 15, where the veneering overlay is intended to intimately mate to the top surface of the framework.

17. The dental implant framework of claim 16, where in the position of the support posts is based upon the digital data of the tooth and gingiva contours.

18. The dental implant framework of claim 16, where the veneering overlay and dental implant framework are fully parametric and easily edited during a design phase.

19. The dental implant framework of claim 18, where the veneering overlay and dental implant framework features are dependent upon one another, wherein the dependency allows for changes in orientation, dimensions or features in either the veneering overlay or dental implant framework, and the changes will result in modifications in either the veneering overlay or dental implant framework, whichever was not changed.

20. The dental implant framework of claim 16, where the veneering overlay intended to mate with the dental implant framework includes the gingiva contours captured in the digital data defining the appropriate tooth and gingiva contours for the final dental prosthesis.

21. The dental implant framework of claim 16, where the veneering overlay intended to mate with the dental implant framework includes gingiva contours as designed by an operator.

22. The dental implant framework of claim 16, where the veneering overlay intended to mate with the dental implant framework includes a cutback allowing for a technician to create the tooth or gingiva contours of the final prosthesis.

23. The dental implant framework of claim 16, where the veneering overlay and dental implant framework are permanently fixated to one another by a bonding agent or a mechanical retention mechanism.

24. The dental implant framework of claim 15, where the veneering overlay and dental implant framework can be manufactured simultaneously.

25. The dental implant framework of claim 24, where the dental implant framework is fabricated out of one of the following; titanium or other metallic materials; Zirconia or other ceramic materials; acrylic or other composite materials; a biocompatible material.

26. The dental implant framework of claim 15, where in the digital data defining the appropriate tooth and gingiva contours are derived from one of the following; scanning a diagnostic wax up or denture tooth set up; CAD models in a virtual set up; an intraoral scan of a diagnostic wax up or denture tooth set up taken in the patient's mouth; a CT scan or series of CT scans of the patient's mouth; a CT scan or series of CT scans with the use of a radiographic stent in the patient's mouth.

27. The dental implant framework of claim 15, where in the digital data for locations of the implants and abutments have been derived from one of the following; scanning the analogs in the stone cast of the patient; an intraoral scan of the implants and abutments in the patient's mouth; digital surgical planning of the proposed implant positions on the basis of a CT scan or series of CT scans; a CT scan or series of CT scans.

* * * * *